(12) United States Patent
Hernandez et al.

(10) Patent No.: US 10,102,599 B2
(45) Date of Patent: Oct. 16, 2018

(54) SYSTEM MANAGEMENT DASHBOARD

(75) Inventors: Albert Hernandez, Tustin, CA (US); Susan Pede, Encinitas, CA (US); Joel Rosenfield, Oceanside, NY (US); Daniel Riscalla, Orange, CA (US); Laszlo R. Gasztonyi, Fairfax Station, VA (US); Ronald G. Gesell, Stone Mountain, GA (US)

(73) Assignee: Compressus, Inc., Austin, TX (US)

( * ) Notice: Subject to any disclaimer, the term of this patent is extended or adjusted under 35 U.S.C. 154(b) by 951 days.

(21) Appl. No.: 13/363,135

(22) Filed: Jan. 31, 2012

(65) Prior Publication Data
US 2012/0130738 A1     May 24, 2012

Related U.S. Application Data

(63) Continuation of application No. 11/944,530, filed on Nov. 23, 2007, now Pat. No. 8,131,562.

(60) Provisional application No. 60/867,148, filed on Nov. 24, 2006.

(51) Int. Cl.
| | |
|---|---|
| G06Q 50/22 | (2018.01) |
| G06Q 50/24 | (2012.01) |
| G06Q 10/06 | (2012.01) |
| G16H 40/20 | (2018.01) |

(52) U.S. Cl.
CPC ............ *G06Q 50/24* (2013.01); *G06Q 10/06* (2013.01); *G06Q 10/0633* (2013.01); *G06Q 50/22* (2013.01); *G16H 40/20* (2018.01)

(58) Field of Classification Search
CPC .... G06Q 10/06; G06Q 10/0639; G06Q 50/24; G06Q 50/22; G06Q 10/0633; G06F 19/321; G16H 40/20

USPC .......................................................... 705/2-3
See application file for complete search history.

(56) References Cited

U.S. PATENT DOCUMENTS

| | | | |
|---|---|---|---|
| 6,574,629 B1 * | 6/2003 | Cooke, Jr. ......... | G06F 17/30017 |
| 2002/0063735 A1 * | 5/2002 | Tamir ................. | G06F 11/3438 |
| | | | 715/745 |
| 2003/0110007 A1 * | 6/2003 | McGee .............. | G06F 11/0709 |
| | | | 702/179 |
| 2006/0109961 A1 | 5/2006 | Mahesh et al. | |
| 2006/0136490 A1 * | 6/2006 | Aggarwal ............. | G06Q 10/06 |
| 2006/0155579 A1 | 7/2006 | Reid | |
| 2007/0043860 A1 * | 2/2007 | Pabari .................. | G06F 9/5072 |
| | | | 709/224 |

(Continued)

OTHER PUBLICATIONS

Nagy et al., PACSPulse: A Web-based DICOM Network Traffic Monitor and Analysis Tool, 2003, Radiographics, 23, pp. 795-801.*

(Continued)

*Primary Examiner* — Joy Poh Ai Chng

(57) ABSTRACT

A system and method for acquiring, compiling and displaying data indicative of healthcare data workflow within an integrated healthcare enterprise simplifies the monitoring and identification of inefficiencies such as bottlenecks in the enterprise. Information gathered from enterprise system components and data files are used to measure individual component performance. System alerts and messaging capabilities allow an enterprise administrator to remedy potential bottlenecks before problems arise. Remedial measures may be programmed into the system to automatically remedy inefficiencies as they are identified.

21 Claims, 30 Drawing Sheets

(56) References Cited

U.S. PATENT DOCUMENTS

2007/0088834 A1* 4/2007 Litovski ............ H04L 63/0272
                                                709/227
2007/0203778 A1   8/2007 Lowson et al.
2008/0140448 A1   6/2008 Hernandez

OTHER PUBLICATIONS

Morgan et al., The Radiology Dashboard: A User's Guide to High-Performance PACS, May 2005, Applied Radiology, pp. 17-21.
Notice of Allowance dated Nov. 2, 2011, mailed in U.S. Appl. No. 11/944,530, pp. 1-147.
Response to Non-Final Office Action dated Feb. 2, 2011, as filed in U.S. Appl. No. 11/944,530 dated Jul. 25, 2011, pp- 1-17.
Non-Final Office Action dated Feb. 2, 2011, mailed in U.S. Appl. No. 11/944,530, pp. 1-24.

* cited by examiner

Fig. 6b

|  | Routing Time | | |
|---|---|---|---|
| Destination Radiologist | Average | Minimum | Maximum |
| M3 Site 1    radman1 | 15 | 10 | 25 |
|                       radman2 | 5 | 4.3 | 6.7 |
| M3 Site 1 | 8.3 | 4.3 | 25 |
| M3 Site 2    radman1 | 15 | 10 | 25 |
|                       radman2 | 5 | 4.3 | 6.7 |
| M3 Site 2 | 10 | 4.3 | 25 |
| M3 Site 3    radman1 | 40 | 25 | 55 |
|                       radman2 | 5 | 4.3 | 6.7 |
|                       radman3 | 5 | 4.3 | 6.7 |
| M3 Site 3 | 22.5 | 4.3 | 55 |
| Overall | 13.6 | 4.3 | 55 |

Fig. 7a

MEDxConnect

Systems Management Dashboard

SYSTEMS | STATUS | SERVERS | STUDIES | NETWORKS | ADMIN

Server [St. Mary ∨]  Patient Name [    ]  Limit [10 ∨]  Size [21 MB ∨]  In Last [1 hour ∨]  Modality [US ∨]  [Find]  [Reset]

| Patient Name | ID | Modality | Study Date/Time | Radiologist | Step | Acquisition To M | | Virtual Worklist | | Rad. Claim | Submit Report | Referring Physician Review |
|---|---|---|---|---|---|---|---|---|---|---|---|---|
| | | | | | | Start Date/Time | Finish Date/Time | Received Date/Time | Retrieved Date/Time | | | |
| | | | | | | | | | | | | |
| | | | | | | | | | | | | |
| | | | | | | | | | | | | |
| | | | | | | | | | | | | |
| | | | | | | | | | | | | |
| | | | | | | | | | | | | |
| | | | | | | | | | | | | |
| | | | | | | | | | | | | |

In Last [5] minutes  [Update ▽]

| Destination | Step | Study Count | Avg Size (Kbytes) | Min Size (Kbytes) | Max Size (Kbytes) | Avg Time (min) | Min Time (min) | Max Time (min) |
|---|---|---|---|---|---|---|---|---|
| StMaryMC | Acquisition to M3 | 30 | 1,193 | 293 | 4,993 | 33 | 18 | 48 |
| StMaryMC | Virtual Worklist | 30 | 1,499 | 99 | 3,999 | 82 | 12 | 378 |
| StMaryMC | Time before Radiologist Claim | 30 | 1,005 | 505 | 3,205 | 49 | 4 | 346 |
| StMaryMC | Time to submit Report | 30 | 1,799 | 999 | 2,499 | 33 | 1 | 54 |
| StMaryMC | Time before referring Physician Review | 30 | 801 | 301 | 2,001 | 35 | 2 | 41 |
| StMainST | Acquisition to M3 | 45 | 2,301 | 801 | 3,051 | 63 | 17 | 76 |
| StMainST | Virtual Worklist | 45 | 1,294 | 794 | 3,044 | 104 | 14 | 304 |
| StMainST | Time before Radiologist Claim | 45 | 2,600 | 1,200 | 3,000 | 218 | 13 | 343 |
| StMainST | Time to submit Report | 45 | 1,603 | 1,203 | 5,003 | 90 | 25 | 232 |
| StMainST | Time before referring Physician Review | 45 | 899 | 399 | 2,999 | 218 | 39 | 305 |

Fig. 9c

MEDxConnect

SYSTEMS  STATUS  SERVERS  STUDIES  NETWORKS  ADMIN

Systems Management Dashboard

⊞ ADD USER

| ID | Name | Last Logon | Email | Cell Phone | Fax Number | Notification Method | Action | |
|---|---|---|---|---|---|---|---|---|
| 11513 | Nathalie Houston | | Nathalie.Houston@pa | 17145632456 | 17145632457 | email | Edit | Delete |
| 11713 | Denzel James | | denz@bevat.com | 15181112812 | 15181112613 | SMS | Edit | Delete |
| 11715 | Patrik Gilbert | | admin@propanz.com | 16565364512 | 16565364713 | SMS | Edit | Delete |
| 11801 | Mary Hankook | | Mary@bevat.com | 14432353364 | 14432353368 | SMS | Edit | Delete |
| 11805 | John Brown | | Alex@lymbis.com | 14432357512 | 14432857512 | SMS | Edit | Delete |

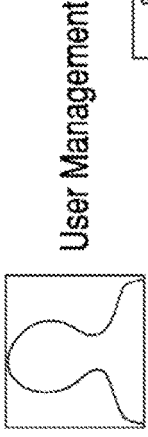

Fig. 9e

MEDxConnect
Systems Management Dashboard

SYSTEMS  STATUS  SERVERS  STUDIES  NETWORKS  ADMIN

⊞ ADD SERVER

| Server Name | Server URL | | Action |
|---|---|---|---|
| StMaryMC | | Edit | Delete |
| StMMainST | | Edit | Delete |
| SMWomenC | | Edit | Delete |
| SMNeorSpec | | Edit | Delete |
| LGRiverview | | Edit | Delete |
| LGCardSpec | | Edit | Delete |
| LuthGen | | Edit | Delete |
| LGPedSpec | | Edit | Delete |

MEDxConnect

SYSTEMS  STATUS  SERVERS  STUDIES  NETWORKS  ADMIN

Systems Management Dashboard

| User Name | Event Type | Event Description | Event Date |
|---|---|---|---|
| admin | user login | user admin has logged to the system | Mon October 18, 2006 (14:51) |
| admin | user login | user admin has logged to the system | Tue October 19, 2006 (16:01) |
| admin | user login | user admin has logged to the system | Tue October 19, 2006 (18:21) |
| system | alert | server admin M3 site 1 back to normal | Wed October 20, 2006 (1:00) |
| system | alert | server admin M3 site 1 not responding | Wed October 20, 2006 (6:24) |
| system | alert | server admin M3 site 1 back to normal | Thu October 21, 2006 (11:17) |

Fig. 9i

MEDxConnect
Systems Management Dashboard

SYSTEMS | STATUS | SERVERS | STUDIES | NETWORKS | ADMIN

⊞ ADD LOCATION

| Name | Description | Address |
|---|---|---|
| St. Mary's Medical Center | St. Mary's Medical Center | Nevada |
| Women's Clinic | Women's Clinic | Colorado |
| Main Street Clinic | Hospital | California |
| Neurology Specialty Clinic | Neurology Specialty Clinic | California |
| Riverview Imaging | Riverview Imaging | Colorado |
| Lucheran General Hospital | Lucheran General Hospital | California |
| Cardiology Specialist | Cardiology Specialist | Colorado |
| Pediatric Specialty Clinic | Pediatric Specialty Clinic | Nevada |

Fig. 11a

Workflow Routing Table

| Column | Type | Description |
|---|---|---|
| RouteID | int | Unique identifier |
| RouteName | varchar(65) | Unique workflow route name |
| Enabled | tinyint(1) | Possible values: (default 1)<br>• 0 – indicates disabled<br>• 1 – indicates enabled |
| ProcedureReason | varchar(65) | Regular expression (default '') |
| FacilityID | int | Ptr to facility in Facilities table (default 0) |
| TimeBased | varchar(16) | Possible values: (default 'None')<br>• None<br>• Period<br>• Daily<br>• Weekly<br>• Monthly |
| StartDate | int(11) | Format YYYYMMDD (default 0) |
| StopDate | int(11) | Format YYYYMMDD (default 0) |
| TimeType | tinyint(1) | Possible values: (default 0)<br>• 0 – indicates All Day<br>• 1 – indicates Start/Stop Time specified |
| StartTime | double | Time in total seconds (default 0)<br>(hours * 3600) + (minutes * 60) + seconds |
| StopTime | double | Time in total seconds (default 0)<br>(hours * 3600) + (minutes * 60) + seconds |
| DayOfWeek | tinyint(1) | Mask for days of the week: (default 0)<br>• 0 bit – no days selected<br>• 1 bit – Monday<br>• 2 bit – Tuesday<br>• 3 bit – Wednesday<br>• 4 bit – Thursday<br>• 5 bit – Friday<br>• 6 bit – Saturday<br>• 7 bit – Sunday |
| FromDay | tinyint(1) | Day of the month (default 0) |
| ToDay | tinyint(1) | Day of the month (default 0) |
| PrefetchStudies | tinyint(1) | Possible values: (default 0)<br>• 0 – do not prefetch studies<br>• 1 – prefetch studies |
| PrefetchReports | tinyint(1) | Possible values: (default 0)<br>• 0 – do not prefetch reports<br>• 1 – prefetch reports |
| PrefetchRouteName | varchar(65) | |

Fig. 11b

Workflow Routes Destination Table

| Field | Type | Description |
|---|---|---|
| ID | int | Unique identifier |
| RouteName | varchar(65) | Unique workflow route name |
| DestType | tinyint(1) | Possible values: (default 0)<br>• 1 – indicates host destination<br>• 2 – indicates group |
| DestinationID | int | Ptr to host in ApplicationEntity table (default 0) |
| GroupID | int | Ptr to group in Groups table (default 0) |

Fig. 11c

Workflow Rules Table

| Field | Type | Null | Key | Default | Extra |
|---|---|---|---|---|---|
| RuleID | int(5) unsigned | | PRI | NULL | auto_increment |
| Name | varchar(30) | | | | |
| TriggerType | int(5) | | | 0 | |
| Enabled | tinyint(1) | YES | | 1 | |
| Rule | text | | | | |
| Comment | varchar(255) | YES | | NULL | |
| SourceAETitle | varchar(65) | YES | | | |
| Modality | text | | | | |
| TimeBased | varchar(16) | | | None | |
| StartDate | int(11) | | | 0 | |
| StopDate | int(11) | | | 0 | |
| CheckDateType | varchar(16) | | | ReceiveDate | |
| TimeType | varchar(8) | | | AllDay | |
| StartTime | double | | | 0 | |
| StopTime | double | | | 0 | |
| DayOfWeek | int(1) unsigned | | | 0 | |
| FromDay | int(1) unsigned | | | 0 | |
| ToDay | int(1) unsigned | | | 0 | |
| ApplyInterval | double | | | -1 | |
| LastRunTime | double | | | 0 | |
| UserId | int(5) | | | -1 | |

Fig. 11d

Sent Images Table

| Field | Type | Null | Key | Default | Extra |
|---|---|---|---|---|---|
| ID | int(5) unsigned | | PRI | NULL | auto_increment |
| FromAETitle | varchar(50) | | | | |
| ToAETitle | varchar(50) | | | | |
| State | varchar(20) | | | | |
| PatientID | varchar(64) | | | | |
| StudyUID | varchar(64) | | | | |
| SeriesUID | varchar(64) | | | | |
| SOPInstanceUID | varchar(64) | | | | |
| Path | varchar(255) | | | | |
| Transfer | varchar(50) | | | | |
| StartTime | double | | | 0 | |
| CompleteTime | double | | | 0 | |
| RetryCount | int(5) | | | 0 | |

Fig. 11e

Received Images Table

| Field | Type | Null | Key | Default |
|---|---|---|---|---|
| ID | int(16) unsigned | | PRI | NULL |
| State | int(5) | | | 0 |
| WorklistState | int(5) | | | 0 |
| PatientID | varchar(64) | | | |
| StuInsUID | varchar(64) | | | |
| SOPInsUID | varchar(64) | | | |
| Path | varchar(255) | | | |
| Transfer | varchar(50) | | | |
| FromAETitle | varchar(50) | | | |
| ToAETitle | varchar(50) | | | |
| DestAETitle | varchar(50) | | | |
| ReceivedTS | timestamp | YES | | CURRENT_TIMESTAMP |

Fig. 11f

Accession Destination Table
- Created after workflow order is filed to keep track of image routing.

| Field | Type | Description |
|---|---|---|
| ID | int(5) | Unique ID |
| AccessionNo | varchar(65) | Accession number |
| DestType | tinyint(1) | ? |
| DestinationID | int(11) | static route |
| GroupID | int(11) | Dynamic route to a group |
| RouteName | varchar(65) | Name |
| FirstSentTS | timestamp | timestamp of first image or report sent |
| LastSentTS | timestamp | timestamp of last image or report sent |

Fig. 11g

PrefetchRoutes Table
- Keeps track of where images should be prefetched from.

| Field | Type | Description |
|---|---|---|
| RouteID | Int(5) | Unique ID |
| RouteName | varchar(64) | Unique route name |
| FromAETitle | varchar(64) | Triggering AET locally for non-workflow rules |
| RemoteAETitle | varchar(64) | Our Prefetch AET listed on remote machine |
| DestinationID | Int(11) | Host ID for remote server we are prefetching from |
| LocalArchiveID | Int(11) | ArchiveID for local machine if it is a local prefetch |
| Days | Int(11) | Number of days old for historical studies |
| SearchBy | Tinyint(1) | 0 for PatientID, 1 for PatName + DOB |
| Enabled | Tinyint(1) | Rule enabled or not |
| PrefetchModel | Varchar(11) | Either Workflow or Simple |
| WorkflowRouteID | int(11) | -1 for non-Workflow prefetch route, otherwise give the routeID listed in WorkflowRoutes |

Fig. 11h

PrefetchPkg Table
- Table used to keep track of historical studies received for prefetching.

| AccesionNo | varchar(65) | Links historical to current study |
|---|---|---|
| StuInsUID | varchar(65) | StuInsUID for each historical study |
| NumOfImages | int(16) | Num of images in historical study |
| NumReceived | int(16) | Num of images received |
| Status | varchar(11) | Pending, Fetched, or incomplete |

SYSTEM MANAGEMENT DASHBOARD

RELATED APPLICATIONS

This application is a continuation of U.S. application Ser. No. 11/944,530, entitled, "System Management Dashboard," filed on Nov. 23, 2007 and now issued as U.S. Pat. No. 8,131,562, which claims priority of U.S. Provisional Application 60/867,148, entitled "System Management Dashboard," filed on Nov. 24, 2006, which is incorporated herein by reference in its entirety. This application is also related to co-pending U.S. patent application Ser. No. 11/944,531, entitled, "Virtual Worklist for Analyzing Medical Images," and U.S. patent application Ser. No. 11/944,534, entitled, "Pre-Fetching Patient Data For Virtual Worklists," both of which were filed on Nov. 23, 2007 and are hereby incorporated by reference in their entirety.

FIELD OF THE INVENTION

The present invention relates to a system and method which provides healthcare enterprise-wide monitoring and analysis of resources and networks and the ability to present graphical and tabular summaries of resource and network activity.

BACKGROUND OF THE INVENTION

Presently, healthcare enterprises generally are plagued by the lack of connectivity and interoperability between disparate hospital and radiology information systems (HIS/RIS) from a variety of vendors. Typical systems may employ a mix of incompatible network, Picture Archive and Communication System (PACS), and diagnostic image format standards, such as HL7, DICOM, IHE, and XML.

The lack of interoperability between existing information and imaging systems is one of the most critical problems facing the diagnostic and management effectiveness of the healthcare profession today. This fundamental problem not only diminishes the potential benefits of medical care capability, it also diminishes the financial bottom line of every healthcare facility. In addition, solving the interoperability problem is essential for eventual implementation of a standards based enterprise wide Electronic Health Record.

By using the IHE (integrating the Healthcare Enterprise) systems integration standards approach with cooperation from customers and vendors, effective and powerful systems integration solutions for the healthcare enterprise, such as the MEDxConnect products by Compressus, Inc., seamlessly integrate a wide variety of independent systems into a single network. For example, the MEDxConnect products use a technique of dealing with messages between disparate systems. This permits the MEDxConnect products to present messages to a vendor workstation or system in a compatible format. Each disparate system has some unique characteristics that are handled by the MEDxConnect System to make the transfer of data transparent.

However, once in place, integrated networks are only as efficient as their weakest link. Many times in a healthcare enterprise there is a bottleneck in communications. Some facilities within the enterprise are overloaded while others are not operated at capacity. In other instances, resources in the form of equipment are not efficiently deployed. Certain geographic locations may have the need for additional resources over other locations. Still in other instances, resources in the form of personnel are not efficiently deployed or working at optimal levels. In most instances, such specific inefficiencies would go largely undetected in a healthcare enterprise because the only way to detect or identify these inefficiencies is to have an administrator review possibly hundreds of tables in logs to find the problem. This is often so time consuming that it can't be done. Consequently, a system is needed which quickly identifies or detects inefficiencies or bottlenecks in the workflow, alerts the administrator to the problem and provides remedies to the problem.

SUMMARY

Various embodiments provide systems and methods for summarily displaying an overview of the status of an integrated health enterprise in a graphical user interface (GUI). The various embodiments assist in identifying inefficiencies or bottlenecks in workflow for an enterprise. In one embodiment a graphical view of various workflow operations to monitor and identify inefficiencies is provided. In a further embodiment, a system and method is provided which enables a system administrator to find and correct bottlenecks in order to make the enterprise more efficient. In yet a further embodiment, a system and method is provided which enables a system administrator to efficiently deploy resources. Still further embodiments provide maintenance and administration tools that permit enterprise support personnel to quickly find and respond to enterprise system problems before they become a crisis and are reported by users. The embodiments provide a proactive system information tool for administrators of a healthcare enterprise.

Embodiments may also provide tools for monitoring and managing efficiency overall for an enterprise, such as an association of hospitals and clinics. Embodiments may include layered software solutions that are configurable, scalable, expandable, and affordable. Embodiments may support any or all established or emerging standards for information formatting, transmission, and storage and for image compression.

BRIEF DESCRIPTION OF THE DRAWINGS

The accompanying drawings, which are incorporated herein and constitute part of this specification, illustrate embodiments of the invention, and, together with the general description given above and the detailed description given below, serve to explain features of the invention.

FIG. 6b portrays an example of additional server status detail.

FIG. 7a portrays an example of a tabular display summarizing a study status.

FIG. 9c portrays an example of a display of the authorized users.

FIG. 9d portrays an example of a display of the various fields associated with each authorized user.

FIG. 9e portrays an example of a display showing the list of available servers connected to the network.

FIG. 9f portrays an example of a display of the Add a server screen where additional servers and information regarding the new server may be entered.

FIG. 9h portrays an example of a display of the possible logging options available to an administrator.

FIG. 9i portrays an example of a display of the possible location options available to an administrator.

FIGS. 11a-11h provide example data structure diagrams of records of a database describing routes, destinations, rules, received images, accession destinations, and sent images.

DETAILED DESCRIPTION

The various embodiments will be described in detail with reference to the accompanying drawings.

Efficiency of workflow in a healthcare enterprise is very important to the healthcare delivery system. With doctors and diagnostic equipment in high demand and ever increasing pressures on healthcare institutions to control costs, it is very important to maintain highly efficient workflow across the healthcare enterprise. In order to achieve high efficiency, an enterprise must be able to monitor the workflow among users, critical systems and equipment, data storage facilities, etc. If an enterprise is properly monitored, instances of inefficiency, resource failure or improper deployment of resources can be detected and identified. However, such detection requires rigorous and intensive review of system status and is not readily detected and identifiable. In addition to the high demand placed on doctors and equipment, the modern integrated healthcare enterprise features several elements which increase the challenge facing a system administrator charged with managing the enterprise system. These include a large number of different, sophisticated, stand alone diagnostic imagers (e.g., X-ray, CT scanners, PET scanners, MRI scanners), and different labs and examination rooms—each with their own data formats, communication protocols and user interface. In particular, image studies using one or more types of medical diagnostic imagers (sometimes referred to herein as "modalities") generate large volumes of image data, with different types of imagers generating different types of image data, all of which must be routed, stored, displayed and managed efficiently by the enterprise system. This complicated network of data sources is connected to hundreds of user stations and computers which must be accessed by hundreds of users, both resident and transient. This combination of high complexity, endemic hardware/software incompatibilities, high user demands and expectations, and the urgency and criticality of medical services depending upon the network places unique demands on the enterprise system and particularly the system administrator not met by known enterprise system tools. Accordingly, there is a need for system administration tools capable of helping the healthcare system administrator manage and optimize the integrated healthcare enterprise system.

An embodiment can be configured as some combination of hardware and software providing seamless connectivity between all image acquisition, PACS, and HIS/RIS systems within a healthcare enterprise. An embodiment is built upon an underlying infrastructure of components which work together to enable an interoperable enterprise healthcare system. The infrastructure may be composed of existing networks, servers, information systems, imaging systems, and application software. A simple example of such an enterprise healthcare system is shown in FIG. 1.

Figure 1:
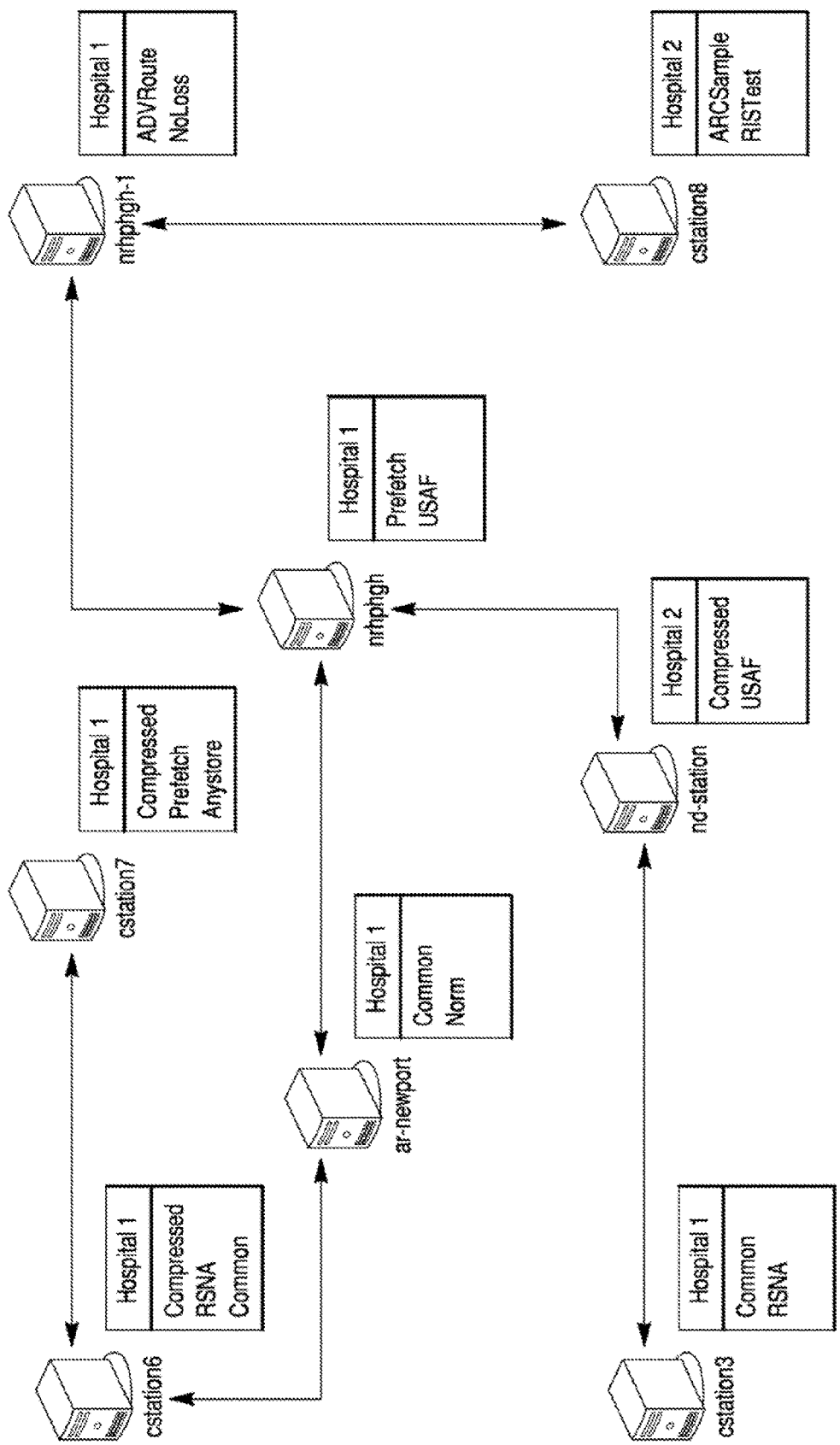
FIG. 1 is a schematic diagram of a small network of workstations linked by any of various hardware and communications protocols.
Figure 2:
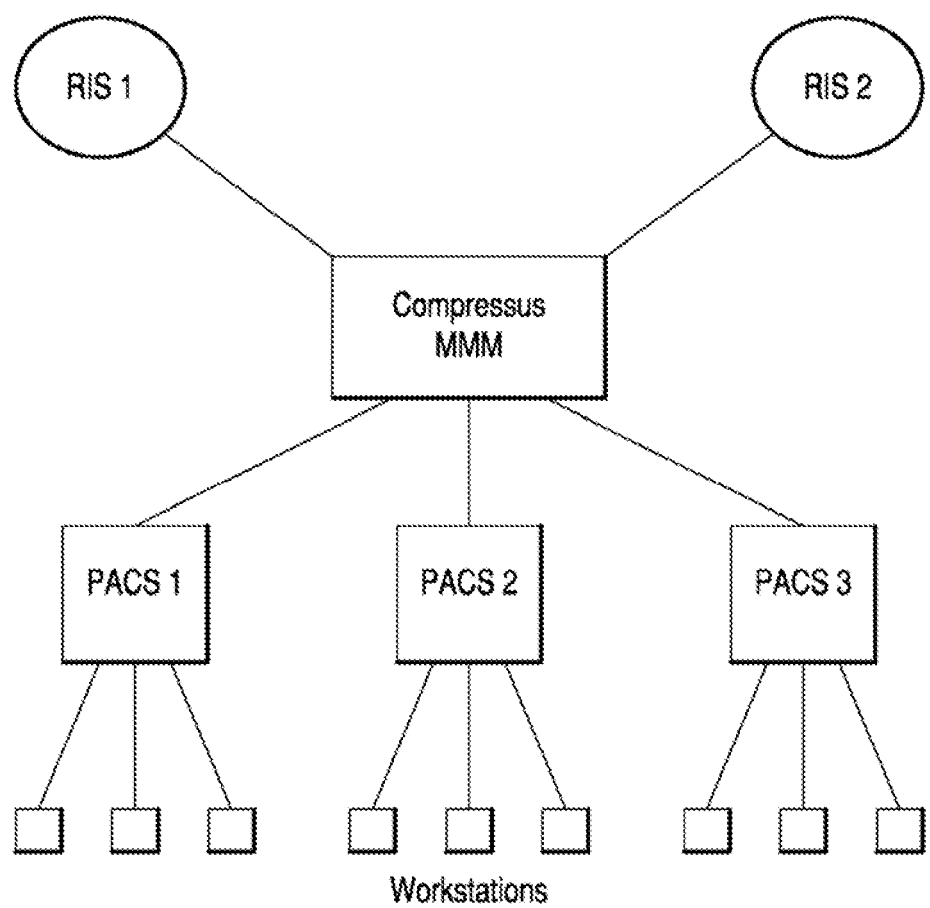
FIG. 2 is another schematic diagram of a small network of workstations.

FIG. 1 is a schematic diagram of a small network of workstations within an enterprise healthcare system linked by any of various hardware and communications protocols, such as Ethernet, TCP/IP, Internet, wireless IEEE 802.11, or other technologies of the future. FIG. 2 is another schematic diagram of a small network of workstations within an enterprise healthcare system.

The underlying infrastructure of the enterprise healthcare system may be augmented with software (and further computer hardware as necessary) to solve the interoperability problem. Such an augmented, integrated, "Interoperable Network" may adhere to and translate between accepted medical data and communications standards including HL7, DICOM, IHE, and XML. The augmented Interoperable Network can leverage existing communications infrastructure to interconnect existing information subsystems and applications through standardized and proprietary formats. The augmented, Interoperable Network may also provide intelligent auditing of the workflow between subsystems. The Interoperable Network uses the communications protocols and semantics of each participating networked information subsystem, server, and imaging workstation. The Interoperable Network may mediate interoperability between different applications, creating a virtual integrated enterprise wide information system that adheres to the IHE technical framework.

An integrated healthcare solution embodiment, such as the MEDxConnect Medical Message Mediator ($M^3$) by Compressus, Inc., will acquire the enterprise information needed for efficiency analysis from its connection on the network. Information from all HIS/RIS/PACS and other systems involved with the diagnostic process will be stored on the M3. Use of various standardized messaging and the MEDxConnect Bloodhound Technology by Compressus can provide the acquisition of the information.

The enterprise information data can be stored in the M3 virtual working storage in various tables. This data can be maintained and updated as new information is available to the M3. This data can then be used for compilation and display, according to user selections and criteria, on the monitoring solution of the various embodiments.

Difficulties in diagnosing the health or performance status of an integrated healthcare enterprise system are not the result of a lack of data or information. In contrast, the difficulties result in part from an overabundance of data to review. Once a system administrator has had the opportunity to review all of the relevant data, the health or performance status of the system has already changed. The challenge is to gather and show the information in a manner that allows the administrator to gauge workflow and identify the problems quickly. If an administrator has to look at potentially hundreds of screen log pages on a monitor or hundreds of hard copy log pages, it is difficult, if not impossible, to accurately examine and assimilate the data. It is very demanding to use these log based tools to measure the workflow efficiency of the enterprise. Further, such a review is not in real time, and thus any conclusions reached will be related to a system state that may no longer be present or of concern. Accordingly, a system and method to expedite, simplify and summarize the profusion of data representing the overall status of an integrated health enterprise system is desired.

An embodiment of the present invention automatically gathers healthcare enterprise workflow information from the network messaging associated with the workflow and makes it quick and easy for an administrator to view and assimilate the information in order to analyze workflow efficiency and make appropriate changes. Embodiments of the present invention provide a "dashboard" display which quickly and graphically displays a number of parameters for fast recognition of system status. For example, the Compressus, Inc. MEDxConnect Systems Management Dashboard (SMD) implementing an embodiment provides the needed overview in monitoring healthcare enterprise activities.

An embodiment provides software tools for collecting, analyzing and compiling healthcare enterprise workflow information. Data regarding system and resources, particularly data on systems and resources unique to the healthcare enterprise, are collected by the data acquisition unit. The embodiment then gathers and analyzes the workflow package for presentation to a user.

An embodiment displays workflow activity and summaries that are selected by the user. The display may be presented on a web client using a browser on a Windows based (or similar graphical user interface) workstation by a user with an administrator log-in. Categories of workflow activity and healthcare data characteristics involving HIS, RIS and PACS systems may be available for display and analysis. The specific categories of workflow activity and healthcare data characteristics available depend upon the user's desires and availability of data.

The embodiment application may be accessed using secure socket connections (https) to maintain a high level of interaction security with the users, thereby ensuring a reasonable level of protection from possible eavesdroppers and "man in the middle" security attacks.

The various embodiments use graphical displays to show representations of sessions between the devices that comprise the healthcare enterprise network. This permits the embodiment to be a DICOM, HL7 or other standards heartbeat monitor of information between the multi-vendor systems that participate in the integrated healthcare enterprise system. The suggested graphical user interface (GUI) of an embodiment may be built similarly to an existing web application called eStation (now known as MEDxConnect's Clinical Mediator Module) using a Flash/Flex platform to provide graphical and animation capabilities.

The various embodiments display parameters related to HIS/RIS/PACS data traveling across the healthcare enterprise network that are connected to the data acquisition unit. The embodiments can work as a monitor for all HIS/RIS/PACS data available to the data acquisition unit. The embodiments work to can augment HIS/RIS/PACS system usage by the customer. The embodiments may permit the customer to monitor activities, track the routing history of a healthcare data, find workflow inefficiencies and make appropriate corrections across the healthcare enterprise network. For example, the embodiments may monitor and display: routing times, how many studies are sent to each destination, system errors, routing retries, routing failures, etc. The categories of monitored information may be viewed in tabular format and/or a graphic format.

The embodiments include effective displays for presentation of healthcare enterprise system information to a user. As an example, an embodiment aggregates various metrics of the healthcare enterprise system operation to measure overall system performance. It then presents the system performance measurements to the user in an easy to assimilate manner on a display. Specific embodiment displays are dependant upon appropriate information and customer set criteria. For example the information can be organized and displayed by:

1. Studies completed by day, week, or other time base parameters, and then by:
    Modality,
    Diagnostic physician,
    Referring physician,
    System wide;
2. Aging of studies by:
    All studies,
    A time range specified by year(s) or month(s);
3. Storage parameters: how much space is being used by studies and at what locations (archives if more than one) by:
    All archives,
    Specified archive(s);
4. Average, minimum and maximum routing times for studies by a specified route;
5. Turnaround time (from study order to report received) for studies by:
    System wide,
    Modality,
    Diagnostic physician,
    Referring physician,
    Department (or other grouping, such as Neuro-Radiology, etc.),
    Patient Study Status (check the status of the assembly of the work package of any patient study that is in process).

Such information may follow each individual healthcare data in a workflow package file which is generated to record all relevant information regarding each healthcare data. In addition, the workflow package file may contain additional information such as metadata markers which indicate the virtual path the healthcare data has taken through the healthcare enterprise system. Such metadata markers may indicate the imaging data source, which servers and workstations have accessed the healthcare data and how long the healthcare data file spent at various components within the healthcare enterprise. In this manner, embodiments of the present invention are able to track the healthcare data through out its residence within the healthcare enterprise system.

Figure 3:
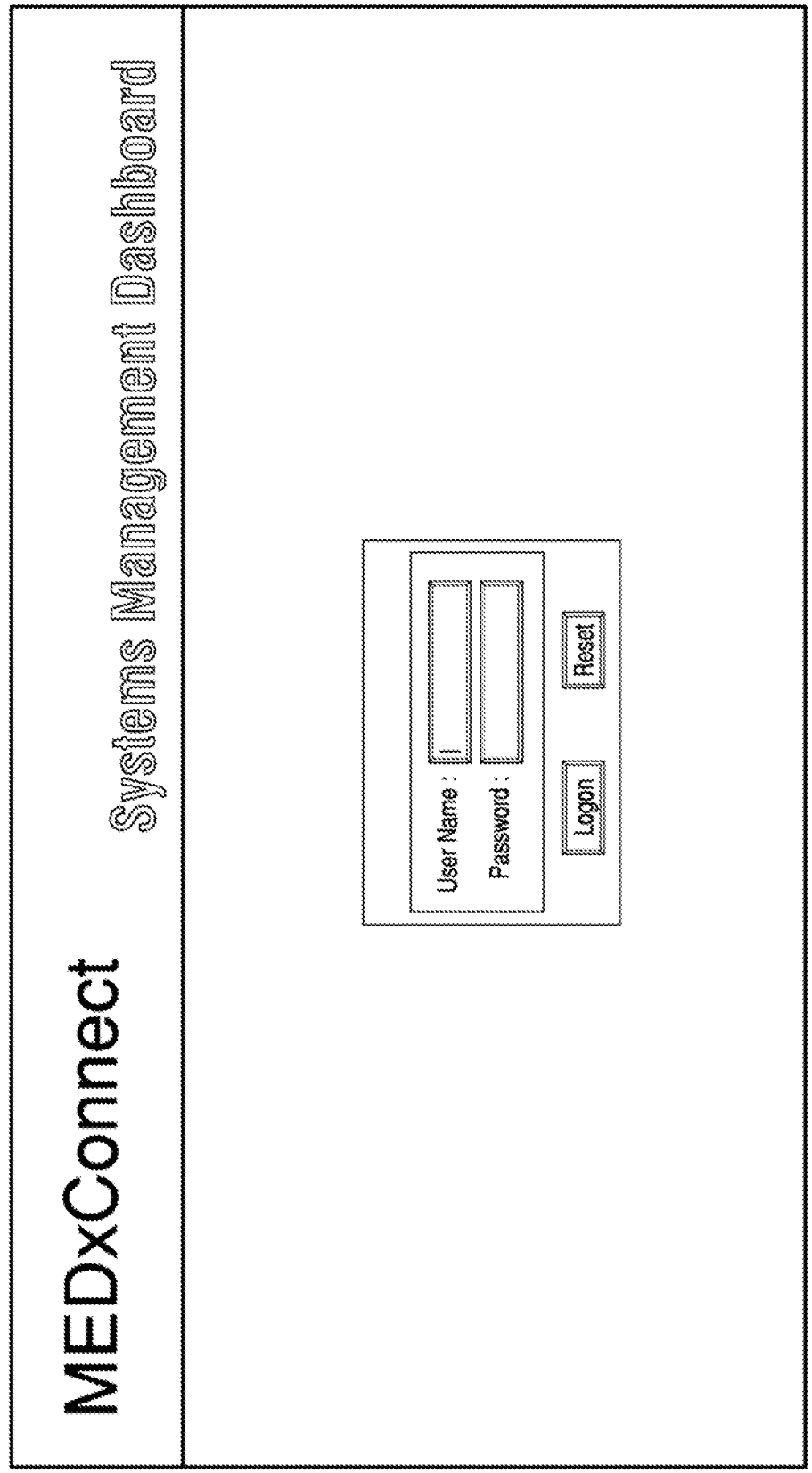
FIG. 3 portrays an example of a login screen.

FIG. 3 illustrates an example of a login screen according to an embodiment. The login screen of FIG. 3 will allow the administrator user (administrator) to obtain access to the embodiment invention application. The administrator will need to provide a correct username and password combination before being granted such access. Logged in administrators will be automatically logged out of the system after being idle for a predetermined number of minutes. The precise number of minutes can be customized in the general settings page described in more detail below. The process of logging into the system should not exceed a time frame of about 20 seconds for optimal security. Embodiments include an administration log-in for all users of the system. Use of the system may be restricted to certain users and not accessible by the general population of the enterprise.

Figure 4:
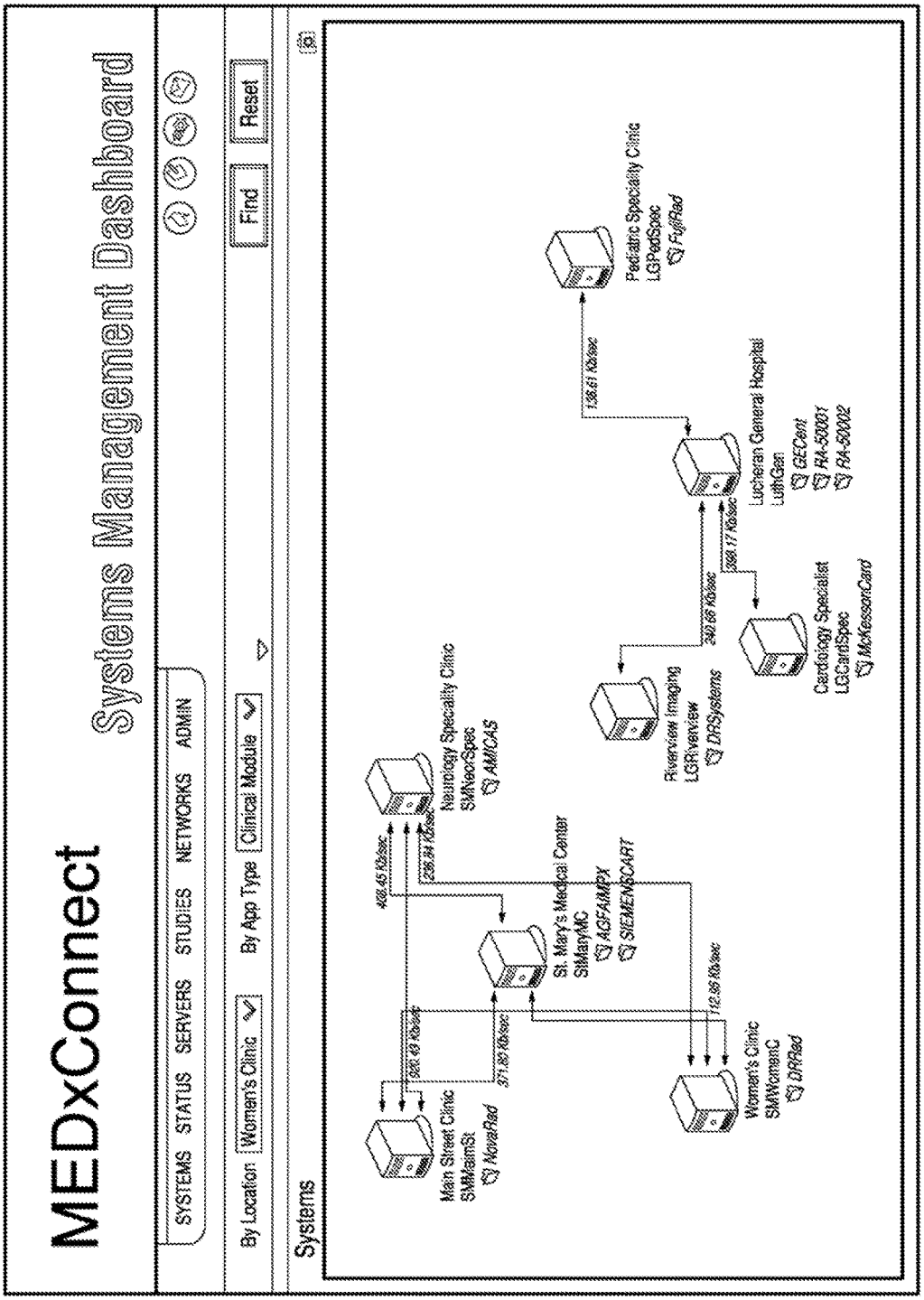
FIG. 4 portrays an example of a graphical display summarizing the overall system status.

Having logged into the system, the administrator is first taken into the Overall System Status display illustrated for example in FIG. 4. The format of this display is an example of a default display for the embodiment application. At the top of the page may be found different virtual buttons which provide access to the different sections of the Web-based application. These include: Overall System Status (Systems); Status List Overview (Status); Workstation/Server Status (Servers); Study Status (Studies); Network Status (Networks); and Manage (Admin). The information displayed inside these sections may be dynamically updated upon changes occurring to the system. To the right of these virtual buttons are another set of buttons allowing navigation to different application useful to the user, including the Archive Module, the Message Mediator, the Clinical Module, and the Billing System. Clicking on any of these items would open a new browser window allowing the user access to the relevant application. These buttons may be made available throughout the application, regardless of the current tab selected.

FIG. 4 illustrates an example of a graphical display of the Overall Systems Status for an imaginary healthcare enterprise. FIG. 4 illustrates, in a graphical format, the enterprise connections for servers and archives that are being monitored. An administrator has the ability to configure the servers using the display illustrated in FIG. 4. Servers are graphically shown by icons in the display. Servers may be manually added to the system status display by the administrator using software tools inside the Server Management section in the Manage section described in more detail below. Once added, further information regarding each server can be extracted through accessing the database stored on the relevant server. Server connections are shown as links that exist between different servers allowing transfer of records, studies, images, and reports within the healthcare enterprise system. These links can be obtained in the illustrated embodiment through querying the "connectServer's cStation database—Application Entity table", and creating links between every server and its corresponding hosts. Relevant archives are archive names that are shown in the bottom right of each server icon. This list may be retrieved from the "connectServer's cStation database-Archives table" from each server.

In addition, for every server relevant information may be displayed. This information may include the location where you can find the server, the name of the server, the relevant archives utilized by the server, storage/network information, and which studies are being transferred from one server to the other. Storage/network information might include the date/time of the last update of data, the storage capacity of a particular server, the transmission rate for data from a particular server, the received rate of data to a particular server, the devices from which a particular server acquires study images and the links to applications available to a particular server for fast access. Additionally, when a study is being transferred from one server to another, a representative icon may be shown. This icon may be shown moving in the direction of the destination server and may disappear when the study transfer is complete.

The Overall System Status may also include a filtering toolbar shown just below the virtual buttons which allow for the filtering of displayed servers and connections based on one of two criteria. Namely location and application type. The location criterion allows for the filtering of the servers according to where these servers are located. The application type criterion allows for filtering of the servers based upon the applications available to particular servers. The filtering toolbar may be concealed or displayed in accordance with user preference.

In addition the displays may be outfitted with a camera icon. The use of such a camera icon allows an administrator to take screenshots of the current state of the server, links and network status.

As above, the administrator may monitor the overall status of the healthcare enterprise from any workstation/server that he is logged into. An administrator for the healthcare enterprise has the ability to customize and set specific parameters for each component within the overall enterprise believed to be acceptable for that particular healthcare enterprise. The set parameters may be stored in a memory connected to the microprocessor for the logged in workstation/server. The color of each component may represent its current status, for example. This status is obtained through performing a ping operation on the component machine, and checking its return value. The ping operation is performed by the workstation/server that the administrator is logged into and compared to the set specific parameter by the workstation/server microprocessor. Return values can be generated based on any of a number of parameters, including any and all of the data set stored in the workflow package file. For example, a return value may be based upon the number of image studies in the queue of the server waiting to be processed. Alternatively, the return value may be based upon the amount of time required to process each healthcare data in the server. Further, the return value may be based upon the number of image studies residing in the queue of the server that belong to a particular modality. Still further, return values may be generated based upon some combination of the number of studies and/or the time to process studies. By comparing the return value of each individual component within the overall healthcare enterprise, an administrator can determine the overall performance and workflow for the healthcare enterprise system.

Various embodiments allow an administrator to set threshold return values to which individual component return values are compared. The results of this comparison provide the administrator with quick insight as to how efficiently the overall health enterprise is operating. For example, an administrator may set a risk threshold return value to 50 image studies residing in the queue of a server. Thus, if the actual return value from a server indicates that more than 50 image studies are residing in the queue, the administrator will know that some bottleneck has occurred at that particular server. In various embodiments, the administrator may set the risk threshold return value based on the amount of time it takes for the referring physician to receive the report on the healthcare data. In such an embodiment, an administrator may require that all reports on a healthcare data be returned to the referring physician within 30 minutes. This will allow the administrator to know that some bottleneck has occurred if physicians do not receive their reports within 30 minutes.

In both instances the reasons for a bottleneck may be varied. For example, there may be some sort of technical malfunction with the server causing a stoppage or slowdown of processing of image studies. Alternatively, physicians and/or radiologists assigned to the particular image studies residing in the queue may not be efficiently retrieving the image studies for analysis. Still further, there may have been some sort of short term flood of requests causing the bottleneck. In any case, by comparing the return value to a threshold return value, an administrator can quickly identify which resources in the healthcare enterprise are overburdened. By drilling further down, the exact reason for the bottleneck can be identified. Once the problem has been identified, remedial measures can be taken to alleviate the bottleneck. For example, if a server malfunctions or is flooded with requests, automatic routing rules may be generated to route image studies to other components within the healthcare enterprise. Alternatively, if the bottleneck is due to radiologists failing to timely claim image studies, those radiologists could be reprimanded. Still other remedial measures may require the administrator to allocate more component resources to various sites to meet the workflow demand. In any case, the ability to quickly identify bottlenecks and their root causes will greatly assist the administrator.

Graphical representations of the component performance levels can be shown through use of color on the displays. For example, colors can be one of three: green, representing the default color for a server indicating a fully functional server; yellow, representing an overloaded server according to thresholds set by the administrator; and red, representing a machine that is performing poorly according to thresholds set by the administrator. The actual representation of these colors may be shown in a legend on the display, which may show the values set by the user inside the System Alerts section. Colors thus can serve as a means to alert the user of any problem with the healthcare enterprise network.

When a component within the healthcare enterprise nears one or more parameters set by an administrator, the problem spots can highlighted on the dashboard display, such as by being shown in a particular color. For example, in FIG. 4, the server named M3 Site 2 and MMM Site 3 may be shown in green, thus indicating good working order for these servers. In addition, the server named M3 Site 1 may be shown in yellow, thus indicating that the limits set by the administrator are being approached and remedial measures might be suggested to avoid a bottleneck or breakdown. When the enterprise system reaches one or more of these limits, the problem spots can further highlighted, such as shown in a second color. For example, in FIG. 4, the servers named M3 Site 3 and M3 Site 4 have reached the set limits and can be displayed in red. Immediate attention or remedial action is required to alleviate these bottlenecks. By the system graphically displaying the information, the administrator is able to quickly and easily identify a bottleneck. This display easily and quickly draws attention to where the bottlenecks may occur or are occurring. By graphically displaying the relative parameters of the healthcare enterprise system in a data compilation display that can be easily assimilated by the user, problems and inefficiencies can be quickly detected and remedial measures taken. Further embodiment displays may dynamically flash the icon of a server with increased frequency to indicate increasing bottlenecks, such as parameters further exceeding one or more limits set by the user.

In addition, as limits are approached or exceeded, an embodiment may automatically display suggested remedial actions for an administrator to take. Alternatively, revised rules may be automatically generated to permit the healthcare enterprise system to automatically re-route image studies in order to alleviate bottlenecks or inefficiencies in the enterprise.

In various embodiments of the display, the administrator can roll the cursor over each resource to view further information regarding the selected resource. In addition, the administrator can also select specific entries on the display to obtain more detailed information. Such additional information may also be obtained by using one or more of the other tabs. In this manner a user can "drill down" to quickly find and identify the causes of a problem. For example, the user may drill down to obtain more specific information by clicking on each resource shown on the display, in response to which the system and method embodiments access the more specific Status List Overview.

Figure 5:
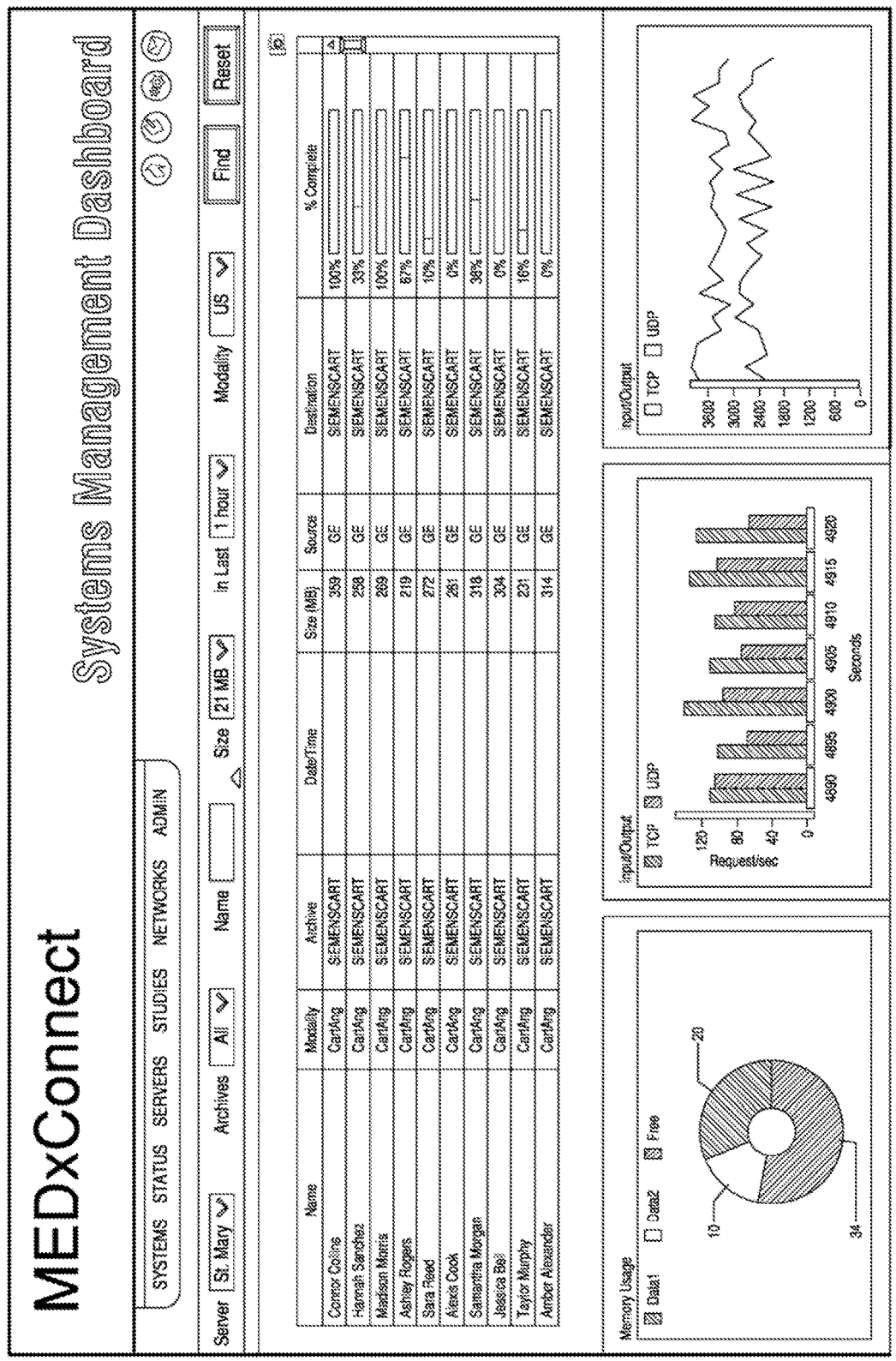
FIG. 5 portrays an example of a graphical and tabular display summarizing an overview of the status list.

More specific information on selected devices and resources may be displayed in the Status List Overview display. FIG. 5 illustrates an example of a graphical and tabular display of a Status List Overview. In the Status List Overview display an administrator can see some details in tabular form, while graphic information about Memory, Input/Output activity and Network activity may also be provided. A filter may also be provided so that the administrator can sort and display more specific information as needed.

In various embodiments, information on enterprise resources, workflow and performance can be obtained from service queries on system servers, from selected data fields and processing of data stored on the servers. Information from these extensive data sources can then be analyzed and audited by the system to provide statistics on enterprise workflow and resource utilization. By correlating data files among all servers within the enterprise, embodiments are able to track each study through its various transmissions and processes, from initiation to completion. By analyzing such study-correlated data gathered for all studies and all resources, usage of resources can be tracked and the performance of individual resources can be audited. Moreover, by tracking the studies in real time, delays in response time can be immediately addressed and corrected.

Usage and capacity of each system server provides insights into these important resources which store and distribute study and image data. Storage capabilities and usage of each server can be obtained through running a Web service on each server, which can return the capacity values for available hard disks and for particular folders on the system (mainly those containing the images, the archives paths). An alternative method (which may be used to avoid installing additional items on servers) obtains "ssh" access to each machine, hence making such queries to the system a rather straight forward task. Examples of the information that can be obtained by such methods include: Storage Capacity (full capacity of the server to store studies); Used Storage (currently used space on the server by studies); and Available Storage (remaining capacity of server which can still hold data.) This server information can be presented to the user by a number of information displays. The "Status List Overview" display illustrated in FIG. 5 displays information relevant to a single server at a time. The user selects the appropriate server from a drop down list and, based on this selection, a list of contained archives can be displayed right beneath the server name (extracted from "connectServer's cStation database—Archives table").

Other sources of resource tracking information are contained within the data fields stored on the servers. Date in the data fields can be stored in a generated workflow package file. Such information is particularly useful in determining the type, size and dates of studies placing demands on the various resources of the healthcare enterprise. By querying the database files on each server, a table can be filled with selected information on the studies contained on the server. For example, the following information may be obtained from the database files and stored in a table:

Patient Name (the name of the patient of this particular study, obtained from "connectServer's cStation database—joining StudyLevel and PatientLevel tables");

Modality (the modality of this particular study, obtained from "connectServer's cStation database—StudyLevel table");

Archive (the archive to which a particular study belongs)

Study Date (the date of this study, obtained from "connectServer's cStation database—StudyLevel table");

Size (the size in MB of this study)—this size can be computed by calculating the size of all images under this study, which can be computed from "connectServer's cStation database—joining StudyLevel and ImageLevel tables" and then grabbing the size of every image through a Web service running on each server which would provide size information (same method used for capacity capabilities);

Study Source (the source from which the study has been obtained)—this information can be the current server at hand since this is where the study is being transferred from;

Destination (the archive to which this study is being routed); and

% complete (which relates to how complete the sending process is). Using the display, a user can select such information from the "Server" drop down menu.

In addition to the data items listed above which may be displayed to a user, embodiments may gather additional information from data fields that are useful for resource tracking and auditing individual resource utilization. For example, data records stored in a server will include data fields storing the date/time that a particular record is received from another server and the date/time that the record is transmitted to another server. The records may also indicate the server from which a record was received and to which the record is transmitted. By correlating information stored in different servers by a common key or data field, e.g., patient name, the routing of studies through each resource and server can be tracked, providing information on processing times, queue delays, and resources employed by the study. This information can then be processed statistically to determine average, peak and minimum values for utilization, processing time, processing steps, and other statistics useful for resource tracking and auditing. This information can then be made available to the user through the display interface.

The administrator can also be given the option to filter studies by different criteria: Limit (sets the number of studies to be displayed at a time, Options include 10 (studies), 20, 50, 100, and unlimited (all studies displayed together); Patient Name (filters the studies based on the name of the patient (or a substring of the name)); Modality (filters studies by modalities, options include selecting one particular modality (US, CR, CT . . . ) or selecting the "(all)" option which shows studies irrelevant of their modalities (shows studies with any modality)); In Last (shows studies within a specific date range, options include "2 days", "4 days", "1 week", "2 weeks", "month", "2 months", "year", and "(any)" which shows studies irrelevant of study dates (shows studies with any date)); and Size (shows studies within a specific size, options include "<1 MB", ">1 MB", ">5 MB", ">10 MB", ">20 MB", ">100 MB", and "(any)" which shows studies irrelevant of their size)

Clicking on the Find button would filter based on the selected criterion, while clicking on Reset Filter would remove all user-modified criterion, and retrieve the original studies based on default criterion. The administrator can also switch between different study pages through clicking on the page number on top of the studies' list grid. The administrator can also type in a page number to move to it by clicking on the Go button.

Also in this screen, the administrator can be given the option to access other RIS applications through clicking, with one machine selected, on one of the applications hosted on this machine from the list automatically updated based on currently selected server. Clicking on any quick link can give the administrator access to the application using the same user/password and open the relevant application in a new browser window.

Figure 6A:
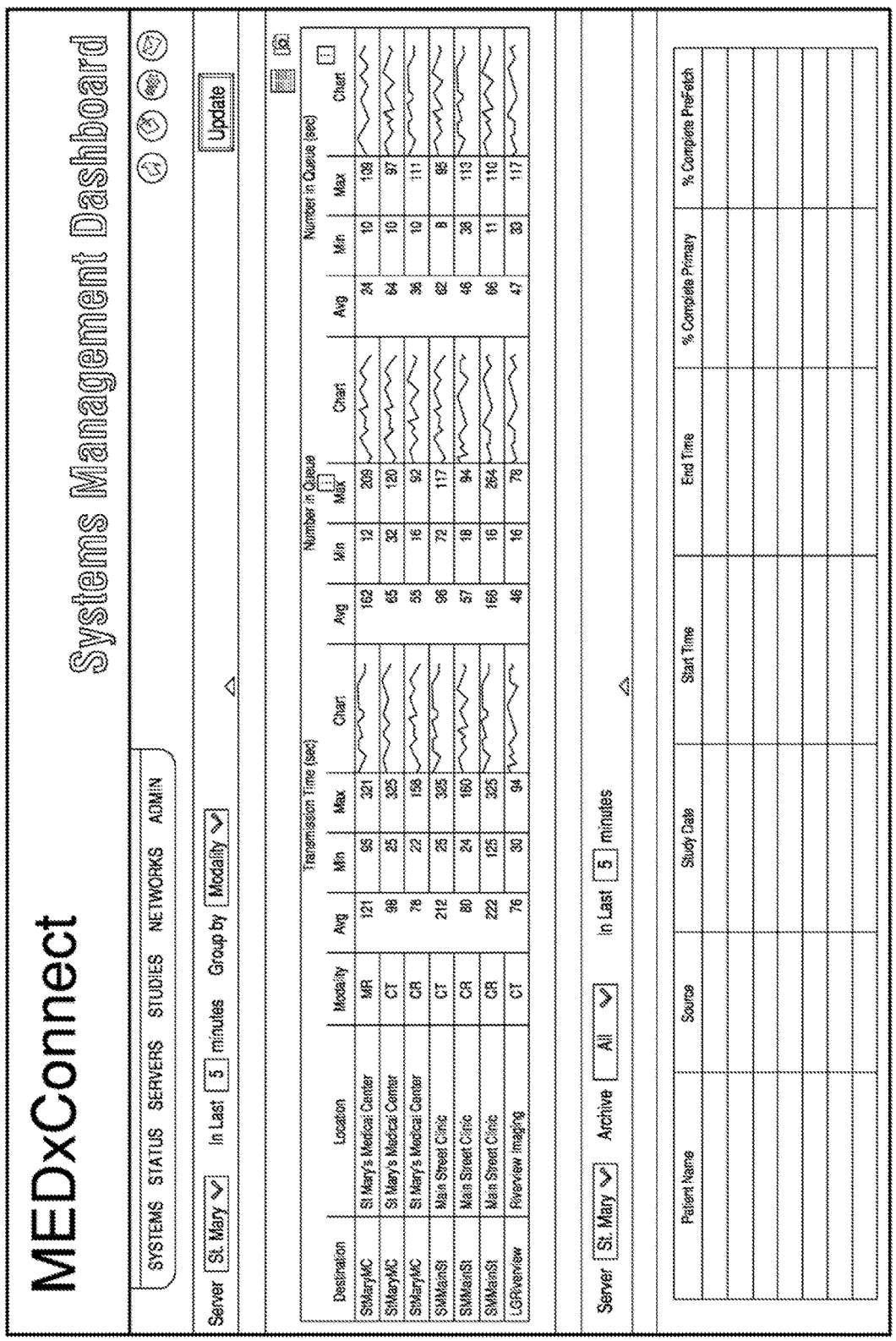
FIG. 6a portrays an example of a tabular display summarizing the server status.
Figure 6C:
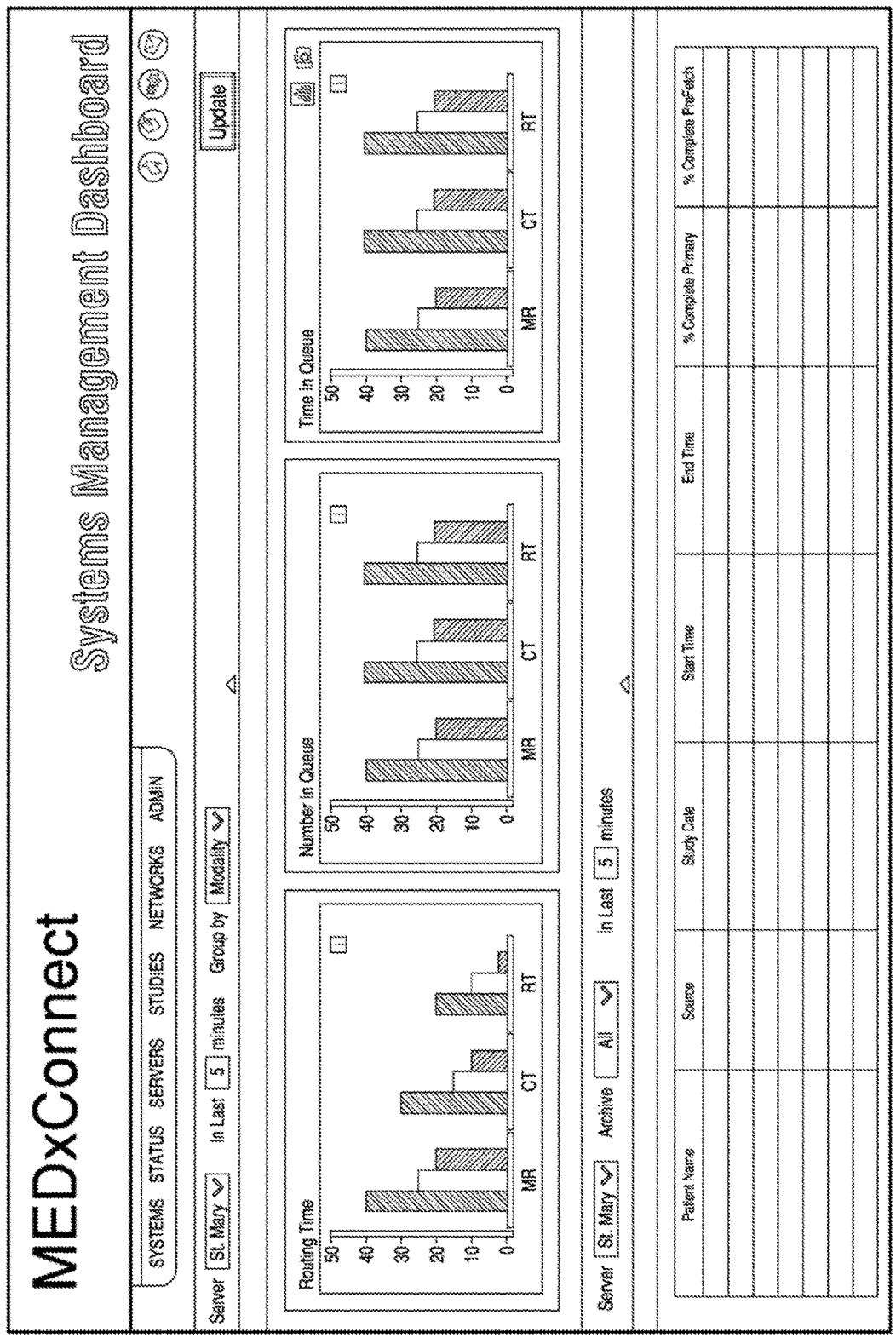
FIG. 6c portrays an example of a graphical display summarizing the server status.

FIGS. 6a-6c illustrate examples of a graphical and tabular display of Workstation Status or Server Status. The Workstation Status display contains information relevant to every workstation's current status. Information comes in two shapes; General view, and detailed view.

In General view, shown in FIG. 6a, statistics on all workstations' status can be displayed. The administrator may be first given the option to specify the time period which is to be the target of these statistics. The first field on top of the display, "In Last", may provide the administrator with the ability to specify in minutes the time span on which the statistics are drawn. As for the details field, it may be used to select a column based on which to summarize relevant information. Options include per "modality", per "group", or per "radiologist" basis. This may be reflected on the displayed column (See FIG. 6a—Tabular View, which shows the Modality column) which will be swapped with the selected criterion (See FIG. 6b—Details Field—Radiologist). Modifying these values and clicking on update may update the statistics displayed below (whether in tabular or graphical mode). These statistics target any or all of the following.

Routing/transmission Time (the time it has taken a study to completely reach a destination in seconds), this is computed as the difference between the start of the transfer process of the study (found under "connectServer's cStation database—SentStudies table as StartTime field"), and the end of the process (found under "connectServer's cStation database—SentStudies table as CompleteTime field"). The Average, Minimum, and Maximum Routing times are displayed, which are computed as averages, minimum, and maximum values overall sent studies (found in "connectServer's cStation database—SentStudies table" with a Sent State).

Number in Queue (the number of studies which are currently waiting in queue to be routed). These studies are the ones found under "connectServer's cStation database—SentStudies table" with a Retrying state. The Average, Minimum, and Maximum numbers are displayed.

Time in Queue (the time spent by studies in seconds waiting in queue to be routed). This information needs to be extracted and saved from the difference between the Total Routing time and the time the study was in a Retrying state. The Average, Minimum, and Maximum times are displayed over all studies.

It may be further possible to display under every destination, a row which displays the summary information for the previous destination with average, minimum, and maximum data for every destination. The last row of the table displays summary information with average, minimum, and maximum data for the whole system including all destinations.

The statistics can be displayed either in a numerical mode (tabular view) or a graphical mode (graphical view). In the tabular view, a numerical results table is displayed showing statistics throughout all the destinations. (See FIG. 6a—Tabular View). The graphical view allows the display of bar chart results for one selected destination at a time. (See FIG. 6c—Graphical View)

The Detailed View of the Workstation/Server Status page offers detailed statistics relative to a selected workstation/server. As shown in FIGS. 6a and 6c, this information is shown in the lower portion of each display. However, the selection may also be completed through two dropdown boxes; one allowing selection of workstation/servers, the other allowing selection of archives relevant to the selected workstation/server. The corresponding table will display information, according to user's choice, that span studies on the particular destination with data relating to any or all of the following (See FIG. 6c—Graphical View).

Patient Name: the name of the patient of this particular study, obtained from "connectServer's cStation database—joining StudyLevel and PatientLevel tables".

Source: where this study is being transferred from, obtained from "connectServer's cStation database—SentStudies table".

Study Date: the date of this study, obtained from the "connectServer's cStation database—StudyLevel table".

Start Time: of the transfer to the server, obtained from "connectServer's cStation database—SentStudies table as StartTime field".

End Time: of the transfer to the server, if it is complete. Found under "connectServer's cStation database—SentStudies table as CompleteTime field".

% Complete Primary: indicates the percentage of completion of the transfer process. This information can be obtained from the "connectServer's cStation database—SentStudies table".

% Complete PreFetch: indicates the percentage of completion of the transfer process. This information can be obtained from the "connectServer's cStation database—SentStudies table".

In the various embodiments, an administrator is provided with graphical information that quickly relates: the routing time of various imaging resources; the number of studies in the queue for a particular imaging resource; or the time a study spends in the queue for a particular imaging resource. As shown, an administrator can obtain fast graphical data for a variety of servers or may filter the data based on modality, group or radiologist. Using such displays, an administrator can determine the cause or source of a bottleneck. The Workstation Status display shown in FIGS. 6a-6c further illustrates additional information that can be displayed related to specific patient imaging studies.

For example, if a delay in the completion of imaging studies occurs, the delay may be due to a variety of reasons. Without sufficient information, an administrator might falsely conclude that there are simply not enough imaging resources to meet the demand. By reviewing the Server Status display, an administrator may be able to determine if there is indeed a legitimate need for additional imaging equipment. However, by sorting the Server Status by group or radiologist, the administrator may discover that there is ample equipment available but the medical personnel are not efficiently completing the imaging studies, thus causing the bottleneck. By identifying the cause of the inefficiency an administrator may be able to correctly diagnose and remedy the true source of the problem.

In addition to presenting data to the administrator which facilitate the investigation of problems, various embodiments include statistical analysis of the data to identify trends and determine when resource usage or performance thresholds are or soon will be exceeded. Such statistical analyses include, for example, determining average and standard deviation values for resource usage, processing time, queue lengths, queue delays, transmission time, etc. by resource, by user, by time of day and day of week, etc. Statistical analysis may also include identifying resources whose performance or usage deviates from the average, users whose actions result in performance or usage that deviates from the average, and the types of studies which result in poor performance or misallocation of resources. Such statistical analysis may also help the administrator identify bottlenecks, the root causes of delays and underutilized resources.

Figure 7B:
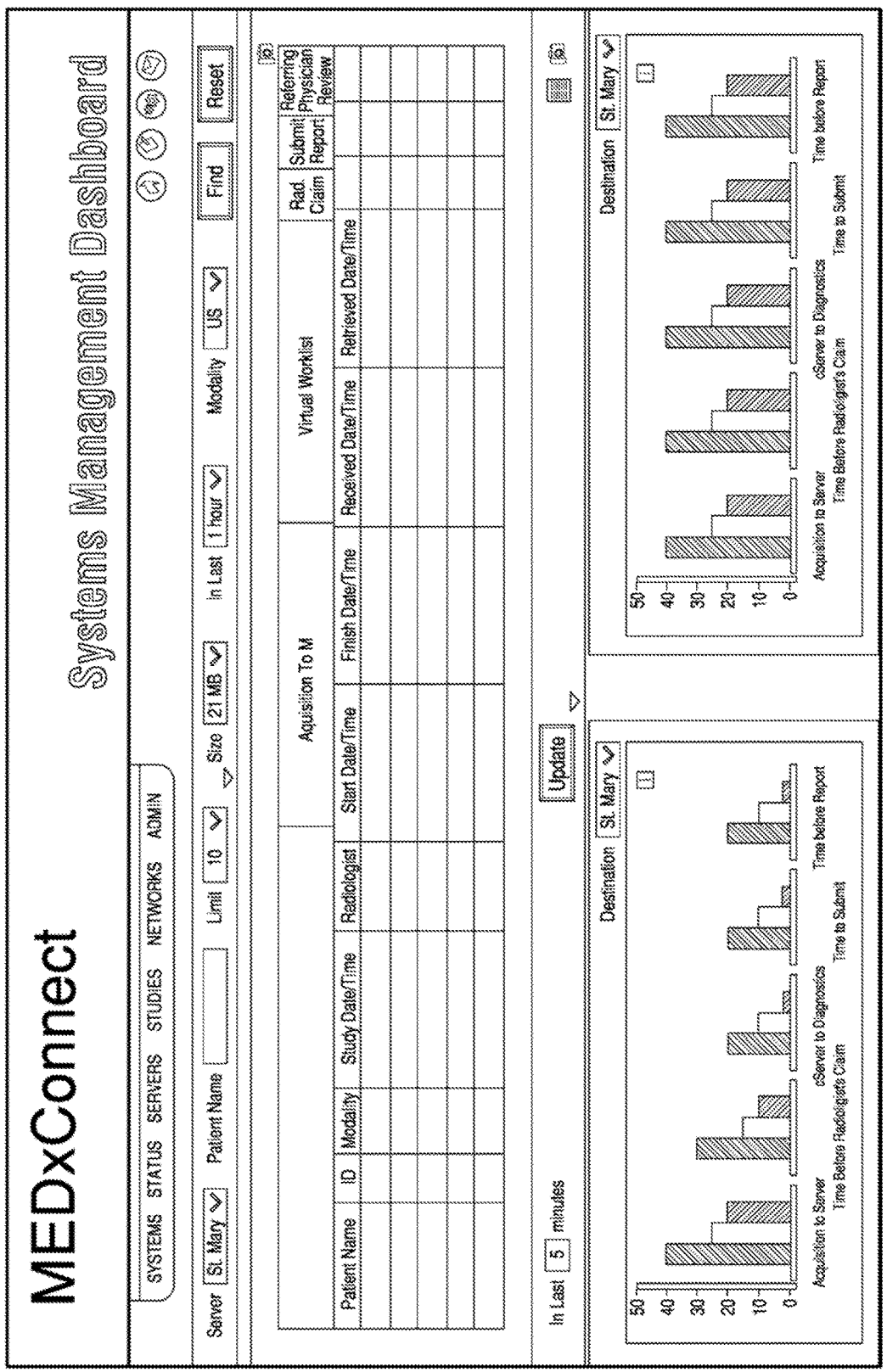
FIG. 7b portrays an example of a graphical display summarizing a study status.

FIGS. 7a and 7b illustrate examples of a graphical and tabular display of Study Status. These displays provide specific information regarding individual patient imaging studies. By analyzing these displays an administrator can determine if a particular patient's review has been efficiently handled. Displayed patient information may include the type of healthcare data, the time and date of the study, who the study was assigned to, and when the study was completed. Such information may provide an administrator with specific insight as to how the workflow of the healthcare enterprise is operating.

The "Study Status" display provides the user with information regarding studies, their turnaround times, as well as relevant statistical information. The display in this section may be divided into two parts, one showing detailed information on a per study basis, and another showing statistical information on a per step basis, with step being one of the following: acquisition to cServer; time before radiologist claim; cServer to diagnostic workstation time; time to submit report (dStation); and time before report received by referring physician. In both FIGS. 7a and 7b, the upper grid displays details concerning all studies at hand. The administrator may filter the studies so that the relevant performance data is displayed. The grid in such displays may contain the following information.

Patient Name: the name of the patient of this particular study, obtained from "connectServer's cStation database—joining StudyLevel and PatientLevel tables".

Modality: the modality of this particular study, obtained from "connectServer's cStation database—StudyLevel table".

Study Date: the date of this study, obtained from "connectServer's cStation database—StudyLevel table".

Acquisition to cServer: The time it has taken the study to be acquired to the cServer. Under this column may be two details; the Received Time at which the study was acquired to cServer (can be obtained from "connectServer's cStation database—StudyLevel table, InsertDate and InsertTime fields), and the Retrieved Time.

Time before radiologist claim: the time is has taken the study before being claimed by a radiologist. Under this column may be two details; the Received Time and the Retrieved Time.

cServer to diagnostic workstation time: the time it has taken the study to be transferred from cServer to the diagnostic workstation. Under this column may be two details; the Received Time and the Retrieved Time.

Time to submit report (dStation): the time is has taken a study since it reached cServer for a relevant report to be submitted against it. This value can be obtained by calculating the difference between received study time (connectServer's cStation database—StudyLevel table, InsertDate and InsertTime, here displayed as the Received Time) and the received report time (connectServer's cStation database—Reports tables, ReportDate and ReportTime, here displayed as the Retrieved Time).

Time before report received by referring physician: the time it has taken a report since it was submitted against a study (the report time, shown here as Received Time, ReportDate and ReportTime, which can be obtained from the connectServer's cStation database—Reports table) until the time it was reviewed by the assigned Referring Physician (ReviewDate and ReviewTime, shown here as Retrieved Time, which can be obtained from "connectServer's cStation database—Reports table").

The statistics can be displayed either in a numerical or tabular mode (FIG. 7a tabular view) or a graphical mode (FIG. 7b-graphical view). In the tabular view a numerical results table shows statistics throughout all the destinations. The graphical view, allows display of bar chart results for one selected destination at a time.

Figure 8A:
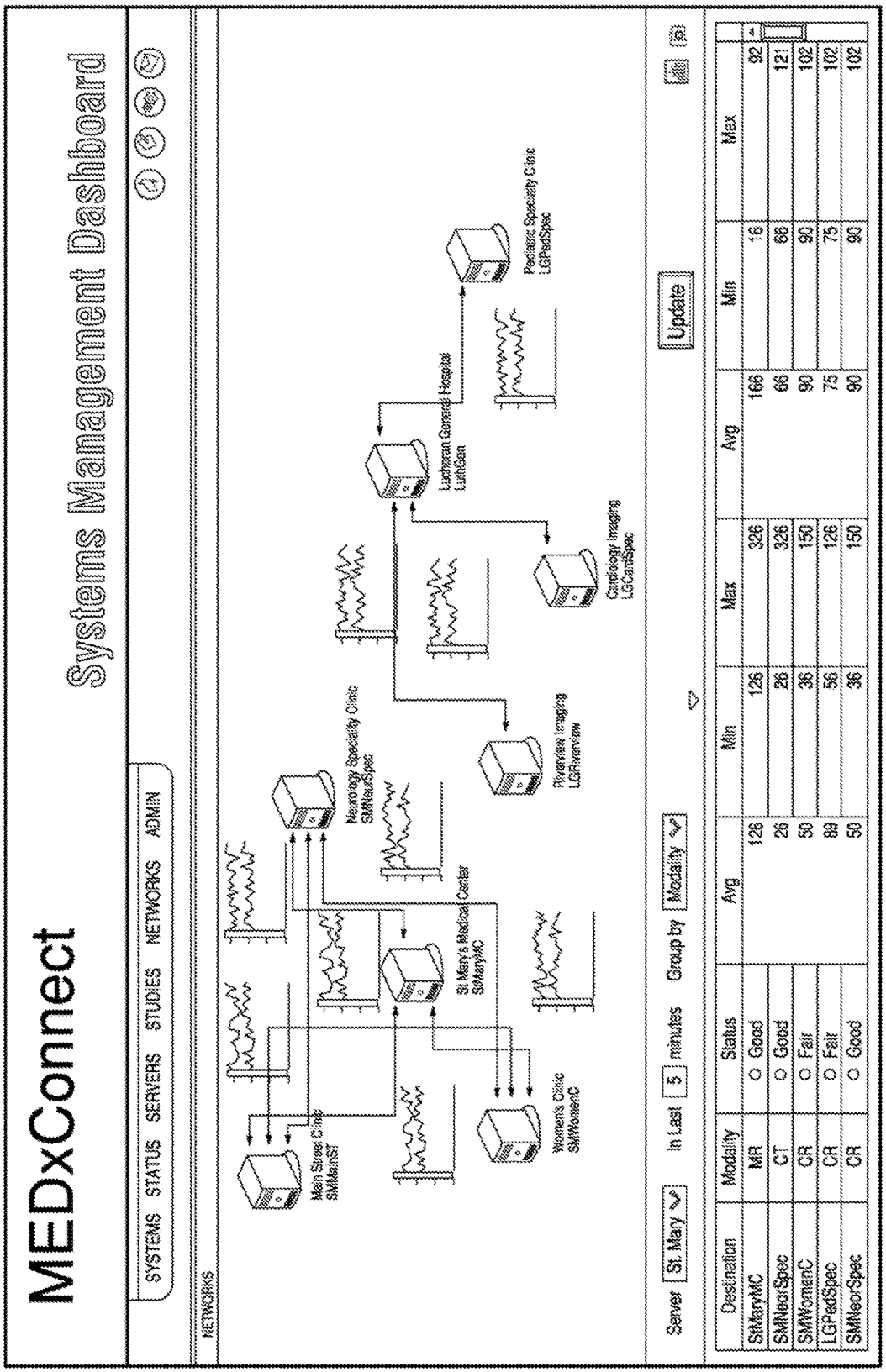
FIG. 8a portrays an example of a tabular display summarizing the network status.
Figure 8B:
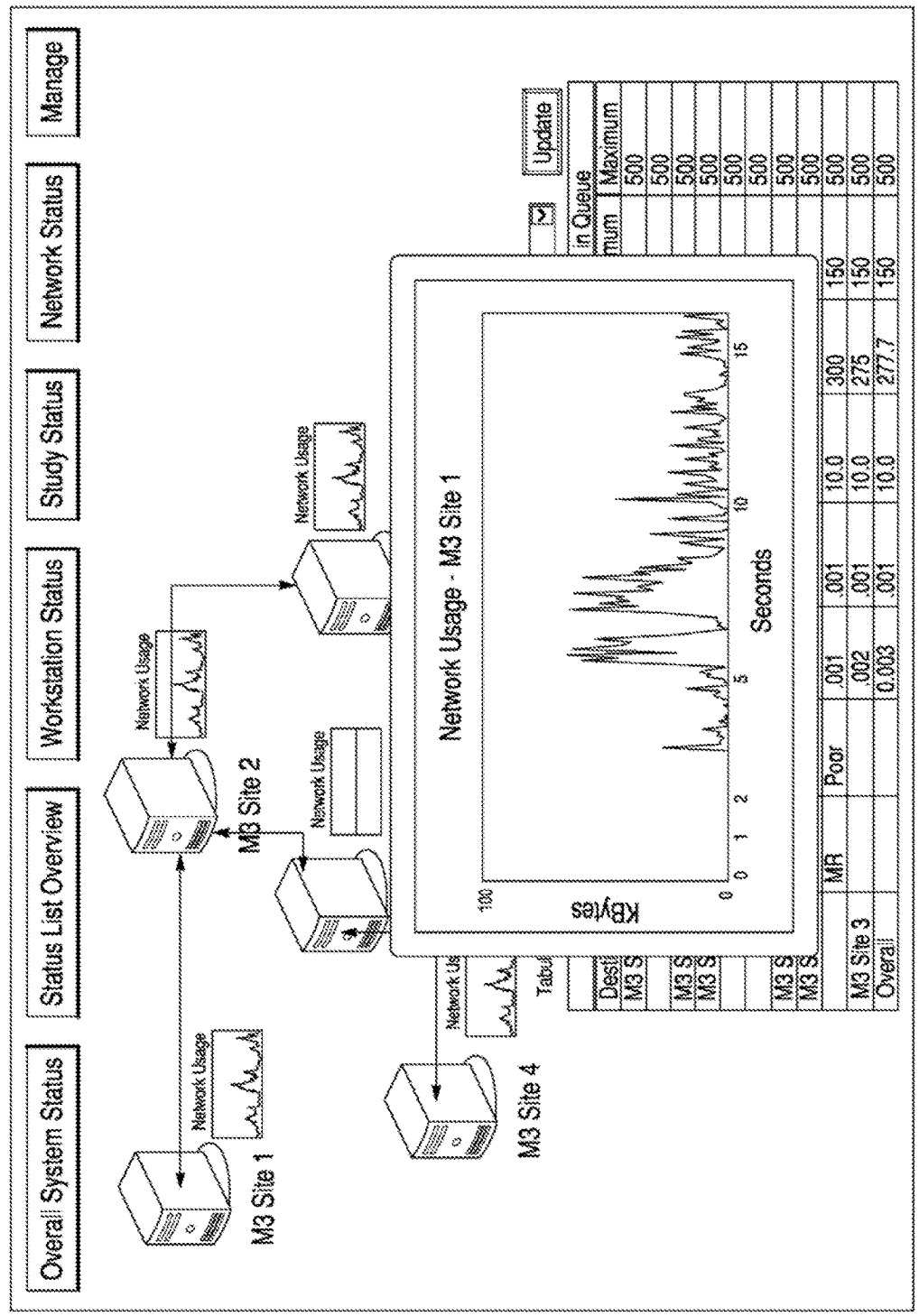
FIG. 8b portrays an example of a graphical display summarizing the network status with a popup.

FIGS. 8a and 8b illustrate examples of a graphical display of network status. Again, by using differing colors, bottlenecks and backlogs can be indicated in the display so they can be quickly identified by an administrator. The administrator can then quickly remedy inefficiencies by re-routing worklists so that workflow is more evenly distributed.

The "Network Status" display contains information relevant to the network status. A graphical representation, similar to the one shown in the Overall System Status (see FIG. 4) may be found in the upper part of the screen. This graph lacks the archive details, but it displays additional information next to every server regarding the network usage in the shape of a graph to the right (for example) of every node, reflecting the real time activity of the relevant workstation, resource or server. Similar to the Overall System Status display, the Network Status display may use colors with the server icons to indicate their current state against threshold limits set in the System Alerts section. Clicking on a small graph can open a popup window displaying, on a larger scale, the details of the network usage for this machine. (See FIG. 8b—Network Status with Popup.) The information shown in this display can be obtained through monitoring, on a fixed interval (refreshing the information every 1 minute, for example), the state of images/studies being sent and received by each server (e.g., percentage sent so far, state of the study/image) and adding a table in memory that registers the current status of the studies being sent/received at each moment. Another embodiment obtains access to each server or workstation through some default user (ssh access) and therefore monitoring the traffic coming in and out of the server.

Figure 8C:
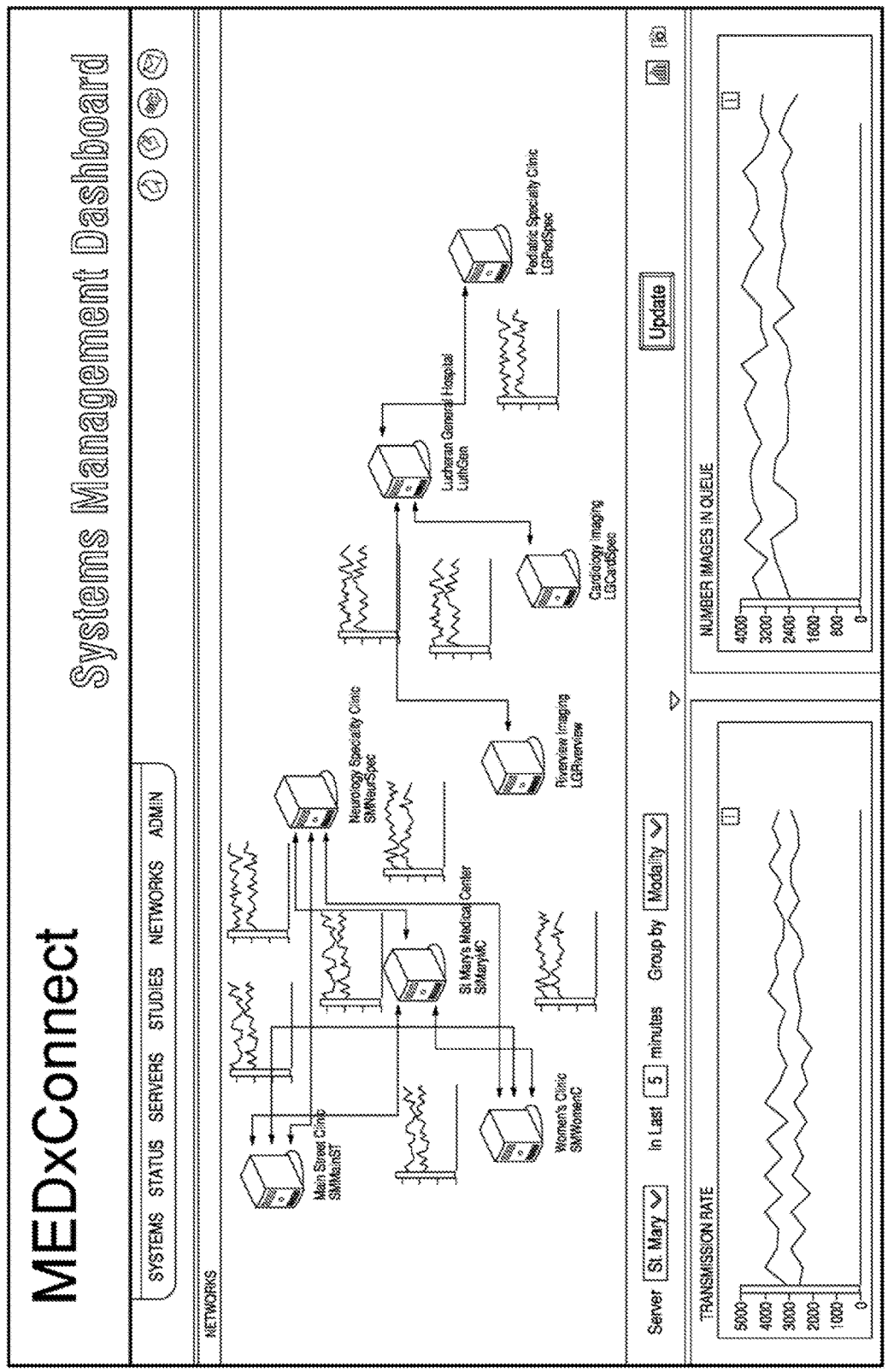
FIG. 8c portrays an example of a graphical display summarizing the network status.

The lower part of the screens shown in FIGS. 8a and 8c contain a display for statistical information regarding network usage. The statistics can be displayed either in a numerical mode (FIG. 8a-tabular view) or a graphical mode (FIG. 8c-graphical view). In FIG. 8a (tabular) the display includes a numerical results table showing statistics throughout all the destinations. In FIG. 8c (graphical) the view includes a display of bar chart results for one selected destination at a time.

The "In Last" field provides the administrator with the ability to specify in minutes the time span over which the statistics are calculated. As for the details field, the "In Last" field may be used to select a column upon which to summarize relevant information. Options include per "modality", per "group", or per "radiologist". This choice will be reflected in the displayed column (see e.g., FIG. 8a—Network Tabular View, which shows a Modality column) which will be swapped with the selected criterion. Modifying these values and clicking on update would update the statistics displayed below (whether in tabular or graphical mode). These statistics may target one or more of the following.

Destination: displays all available destinations.

Modality/Group/Radiologist: available modalities/groups/radiologists under current destination for all studies, based on which statistics will be grouped. Since not all studies have radiologists assigned to them (only studies with submitted reports have radiologists), others will have a <none> option to account for studies with no radiologists. The modality values can be obtained from "connectServer's cStation database—StudyLevel table". The Radiologist values can be obtained from "connectServer's cStation database—StudyLevel table joined with Reports table".

Status: the status of the destination based on the ping replies. Values can be one of three (Good, Fair, Poor) according to set thresholds.

Transmission Rate (Kbytes/sec): the rate at which studies are being sent from one destination to another (archive) in Kbytes/sec. This value can be obtained through dividing the study size by the transfer time. The Average, Minimum, and Maximum values are displayed.

Number Images in Queue: the number of images which are currently waiting in queue to be routed. These images are the ones found under "connectServer's cStation database—SentImages table" with a Retrying state. The Average, Minimum, and Maximum numbers are displayed.

Also under every destination, a row may be added to display the summary information for the previous destination with average, minimum, and maximum data for every destination. The last row of the table may display summary information with average, minimum, and maximum data for the whole healthcare enterprise system including all destinations.

The values in the grid display can reflect the alerts occurring according to thresholds set by the administrator in the System Alerts section. Further, grid cells can be colored, such as with yellow in the case of a mild threshold being surpassed, and with red in the case of a severe alert occurring.

Once logged in, the administrator may be provided with a host of settings that can be edited in order to customize the monitoring and analysis of an integrated healthcare enterprise system. These customization options are provided in the Manage section. The Manage section may serve as a means for the administrator to control and adjust the settings of the monitoring solution. The Manage section may provide control over five main items; User Management (add/edit/delete users), Server Management (adding/editing/deleting servers and their relevant information), System Alerts (setting thresholds, alert types), General Settings (user timeout, logging enabled), and System Logs (event logs).

Figure 9A:
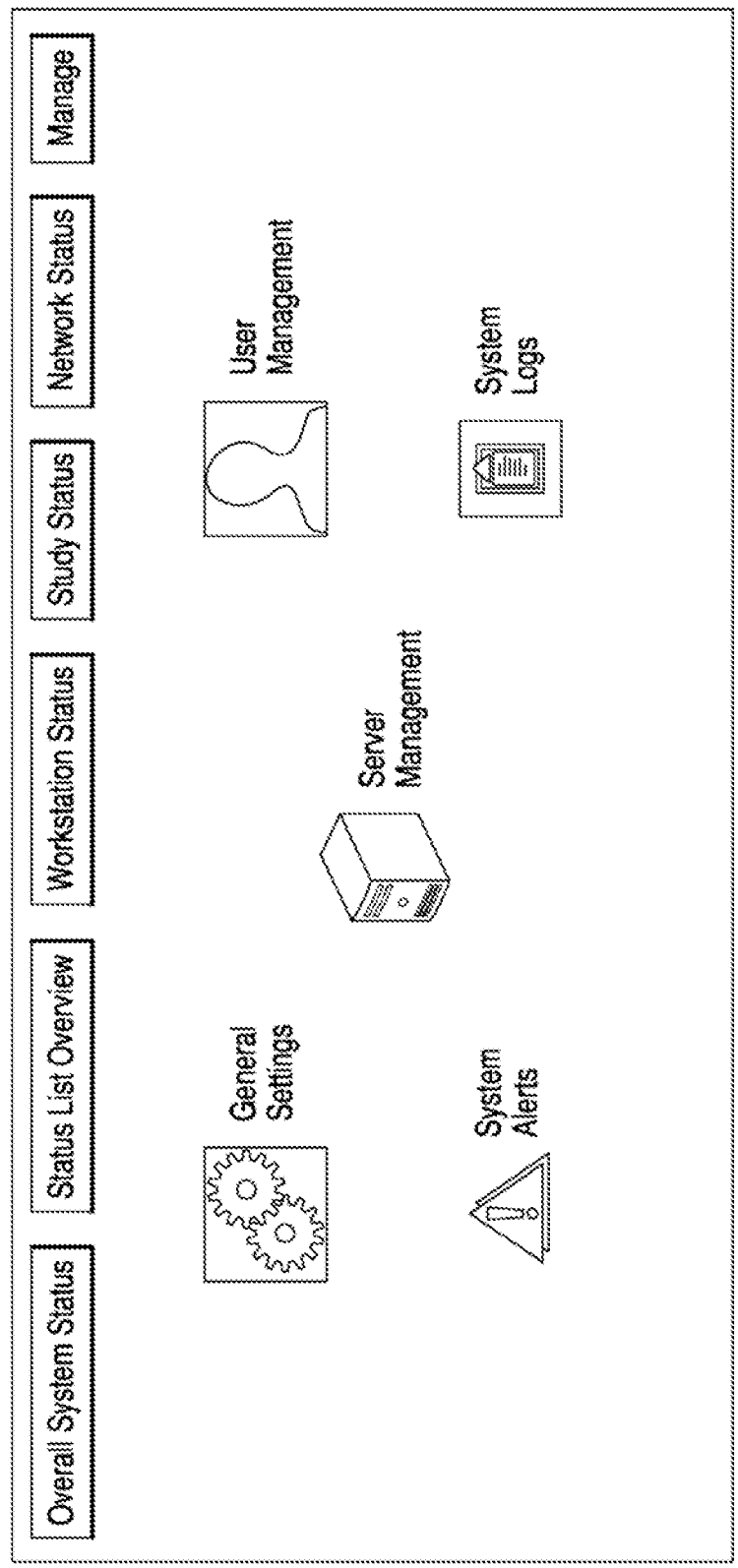
FIG. 9a portrays an example of a Manage section and settings screen.
Figure 9B:
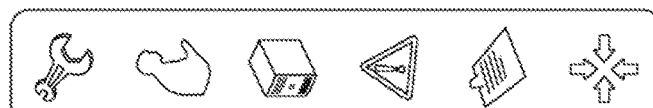
FIG. 9b portrays an example of a display of General administrative settings.

FIGS. 9a-9i illustrate examples for settings and customization options that may be available to a network administrator in the Manage section. For example, under the icon for General Settings, a display of the current settings is shown in FIG. 9b. Such settings may include, for example, whether logging is enabled, how long logs will be retained, how long before a user session is timed out, and various SMTP and SMS criteria, as well as the format for how of sender e-mail and receiver domains are displayed. Upon enabling the "Edit" icon, various pull down menus and editable criteria are displayed which allow the administrator to customize the general settings of the network.

In an embodiment, clicking on the General Settings link will move the icons in an animated manner so that the selected one (General Settings) will show at the top, while the others will become smaller, and show right below it in an aligned manner as illustrated in FIG. 9b. This action can also cause the General Settings section to be loaded. This section is concerned with manipulating general settings of the application. The administrator may be allowed to set any or all of the following.

Logging Enabled: allows the administrator to set whether logging for the system is enabled or disabled.

Clear Logs Older Than: allows the administrator to set the time period in which to keep logs for the system. The possible options include, for example, 1 day (where logs older than one day shall be removed), 2 days, 1 week, 2 weeks, 1 month, and Never (where logs will not be removed).

User Timeout: allows the administrator to set the number of seconds after which a user, being idle, will be logged out of the system (timed out).

Mail SMTP host: indicates the host to use for sending emails.

Mail SMTP requires authorization: indicates whether to use username/password in connecting to the SMTP host.

Mail SMTP user: is the user name to use in case Mail SMTP requires authorization is set to true.

Mail SMTP password: is the password to use in case Mail SMTP requires authorization.

Mail SMTP debugging: allows displaying debugging information regarding email notification (on/off feature).

SMS url: sets the url address being used by a solution in order to send SMS messages.

SMS user name: sets the user name of the account being used to send SMS messages.

SMS password: sets the password of the account being used to send SMS messages.

SMS api_id: sets the api_id of the account being used to send SMS messages.

Fax Sender Email: contains the email of the sender in the account which eStation may use to send faxes.

Fax Receiver Domain: contains the domain used to send fax emails (accounts allowing sending emails would require the fax number to be followed by a certain domain to be used while sending faxes through emails (such as rapidFax, send2fax, trustfax)). The format for sending emails may be <FAXNUMBER>@service_specified_domain. Therefore, this would contain the @ and the domain name provided by service.

The user may customize the operation of the system by altering various fields shown in the FIG. 9b. Once complete, the user may "save" the settings" or "reset" to the original settings.

Under the icon for User Management all active users of the network may be displayed with their contact information. In an embodiment, clicking on the User Management link will load the section concerned with manipulating users. A tabular grid displays information relevant to users, and allows different actions to be performed (Add User, Edit, Copy, and Delete Users). The table displays information which may include: Name, Last Logon (to the system), Email, Cell Phone Number, Fax Number, and Notification Method. FIG. 9c illustrates an example User Management display.

For example, in the display shown in FIG. 9c, clicking on Add User will display input values allowing an administrator to add a new authorized user/administrator (See FIG. 9d). All authorized users can be given all privileges, meaning that all users are administrators. When adding an authorized user, the any or all of following values can be set.

Name: Name representative of the new user. This is a unique identifier of every authorized user, and may be used to login to the system. This field may be required for the creation of the authorized user.

Password: the password for this particular authorized user which may be used to login to the system. This field may be required for the creation of the authorized user.

Confirm Password: a confirmation of the password value provided in the Password field above. This field may be required for the creation of the authorized user.

Email Address: the email address of the authorized user. The format must be xxx@xxx.xxx. In case the selected notifications mode includes an email option, the authorized user will receive notifications to this particular email address.

Cell Phone Number: the cell phone number of the authorized user. The format consists of consecutive digits. In case the selected notifications mode includes a cell phone option, the authorized user will receive notifications to this particular cell phone number.

Fax Number: the fax number of the authorized user. The format consists of consecutive digits. In case the selected notifications mode includes a fax option, the authorized user will receive notifications to this particular fax number.

Notification Method: sets the method that will be used to notify this particular authorized user of any alerts that occur in the system. Options include none (no notifications will be sent), email (notifications will be sent to email address), cell phone (notifications will be sent to cell phone number), fax (notifications will be sent to fax number), all (notifications will be sent using all methods).

In the embodiment illustrated in FIG. 9d, clicking on Save will create the new authorized user as an admin user for the system. Clicking on cancel instead will cancel the creation of the new authorized user, and will move control back to the Manage display. Clicking on Edit will open the same window as the one used for the Add User, but with the data of the authorized user filled and editable. Clicking on Copy user will replicate the authorized user's data, and open an edit Menu to add a new authorized user with this data. Clicking on Delete will pop up a confirmation window to prompt the user to confirm the deletion of this particular user. If the current authorized user confirms this process, the identified authorized user will be permanently deleted.

Clicking on the Server Management icon in the embodiment shown in FIG. 9a will bring up the Server Management display shown in FIG. 9e. As shown in FIG. 9e, in this embodiment administrators are provided with the capability of manipulating which servers and archives are managed/monitored by the system. The administrator is given the option to add/edit/delete servers and their relevant information. The display shows a table with the following information:

Server Name: provides a unique name identifier for each server.

Server URL: identifies the name/ip address of the machine on which the archive is stored.

Action: provides action buttons to either Edit or Delete the server.

Figure 9F:
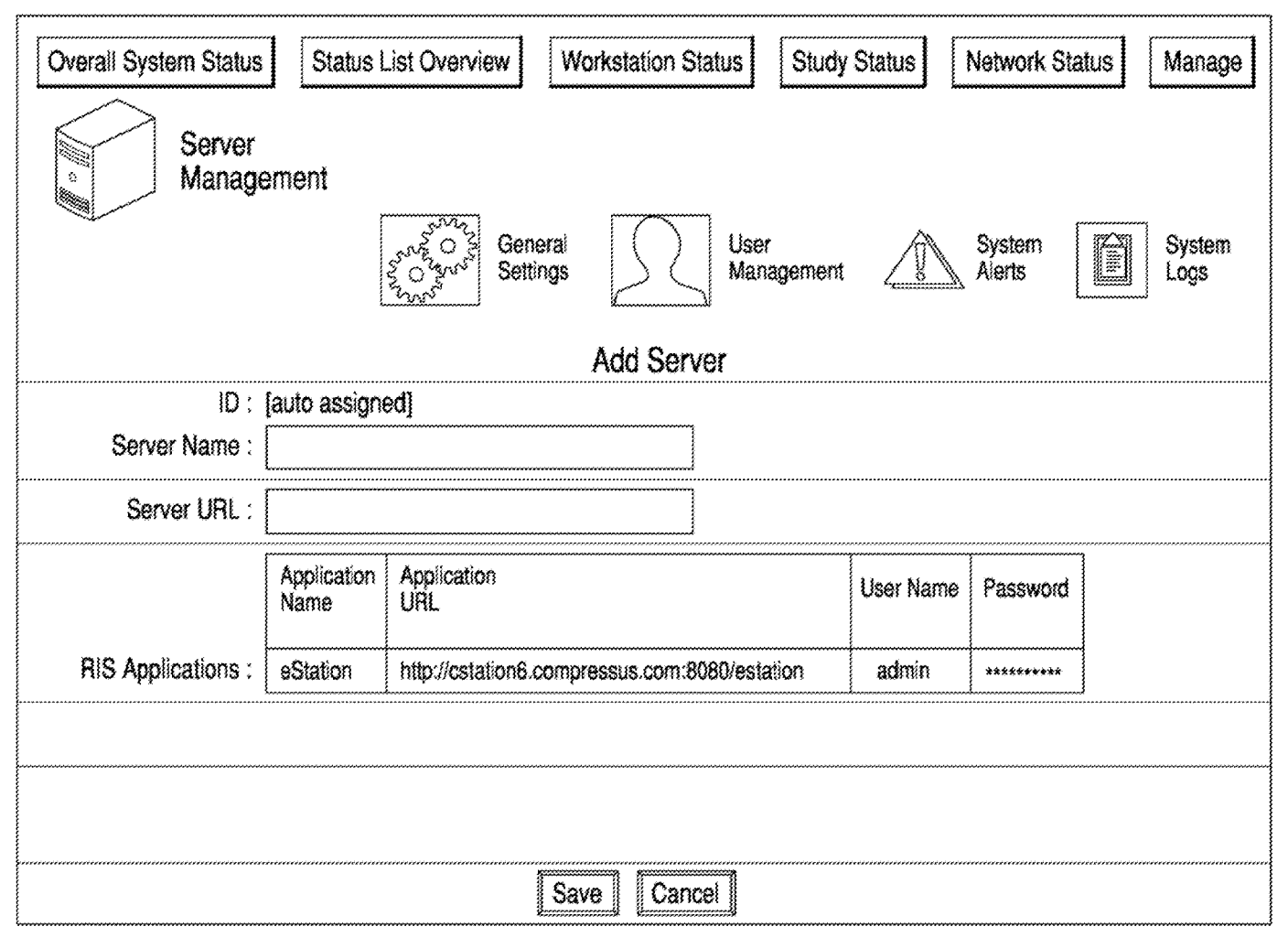

In the various embodiments, an administrator is allowed to Add, Edit, and Delete Servers monitored by the system. By clicking on the Add Server button, the administrator can add a new server as illustrated in FIG. 9f—Add Server. To add a server, the administrator needs to provide some or all of the following information.

Server Name: name identifier of the server.

Server URL: the url/ip address of the server at hand.

RIS Applications: identifies Radiology Information Systems available on every server. The administrator can add RIS applications by providing an application name, application url, username and password to login to this particular application in the editable RIS Applications grid.

The administrator may also be given the option to include information such as SSH username, SSH password, Database port, server description, database schema, database username, and database password. By clicking on Edit, the administrator is allowed to edit information regarding a currently selected server. By clicking on Delete, the administrator is allowed to delete the currently selected Server from the monitoring system after accepting the action in a pop up confirmation window.

Figure 9G:
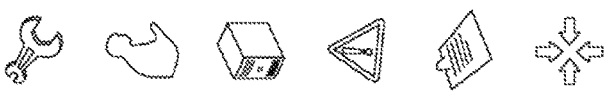
FIG. 9g portrays an example of a display of the possible System Alerts set by an administrator.

In an embodiment, clicking on the System Alerts icon will draw a System Alerts display, an example of which is shown in FIG. 9g. This System Alerts display allows the administrator to configure system alerts in a personalized manner. The administrator is allowed to set enabled alerts, and their corresponding thresholds or limits. Upon the occurrence of an Alert, the administrator will be notified of the alert by email, by SMS, and/or by Fax based on his settings in the User Management section. The user can set Mild (Yellow alerts), as well Severe (Red alerts) alerts to be initiated when certain configurable thresholds have been surpassed. The configurable thresholds may include some or all of the following.

Study Routing:

Average Routing Time: Setting thresholds for this item will cause the grid in the Workstation status to be updated with Yellow and Red highlights in the "Average Routing" column. The administrator can set the mild threshold (Yellow Alert) for this in milliseconds, which will cause a mild alert to be initiated once the threshold has been surpassed. The administrator can also set a High threshold (Red Alert), which will cause a severe alert to be called. The value of the High Risk Threshold must be greater than the Mild Risk Threshold. In the illustrated embodiment, the checkbox next to the item must be selected so that alerts will be set, otherwise, the threshold text boxes will be disabled, and alerts will not take place.

Average Time in Queue: Setting thresholds for this item will cause the grid in the Workstation status to be updated with Yellow and Red highlights in the "Average Time in Queue" column. The administrator can set the mild threshold (Yellow Alert) for this in milliseconds, which will cause a mild alert to be initiated once the threshold has been surpassed. The administrator can also set a High threshold (Red Alert), which will cause a severe alert to be called. The value of the High Risk Threshold must be greater than the Mild Risk Threshold. In the illustrated embodiment, the checkbox next to the item must be selected so that alerts will be set, otherwise, the threshold text boxes will be disabled, and alerts will not take place.

Network Traffic:

Average Transmission Time: Setting thresholds for this item will cause the grid in the Network Status to be updated with Yellow and Red highlights in the "Transmission Rate" column. The administrator can set the mild threshold (Yellow Alert) for this in milliseconds, which will cause a mild alert to be initiated once the threshold has been surpassed. The administrator can also set a High threshold (Red Alert), which will cause a severe alert to be called. The value of the High Risk Threshold must be greater than the Mild Risk Threshold. In the illustrated embodiment, the checkbox next to the item must be selected so that alerts will be set, otherwise, the threshold text boxes will be disabled, and alerts will not take place.

Number In Queue: Setting thresholds for this item will cause the grid in the Network Status to be updated with Yellow and Red highlights in the "Number Images in Queue" column. The administrator can set the mild threshold (Yellow Alert) for this, which will cause a mild alert to be initiated once the threshold has been surpassed. The administrator can also set a High threshold (Red Alert), which will cause a severe alert to be called. The value of the High Risk Threshold must be greater than the Mild Risk Threshold. In the illustrated embodiment, the checkbox next to the item must be selected so that alerts will be set, otherwise, the threshold text boxes will be disabled, and alerts will not take place.

Server State (ping delay): Setting thresholds for this item will cause the Server icons to be updated with Yellow and Red highlights in the "Overall System Status" display. This will also affect the "Status" column in the Network Status grid. The administrator can set the mild threshold (Yellow Alert) for this, which will cause a mild alert to be initiated once the threshold has been surpassed. The administrator can also set a High threshold (Red Alert), which will cause a severe alert to be called. The value of the High Risk Threshold must be greater than the Mild Risk Threshold. In the illustrated embodiment, the checkbox next to the item must be selected so that alerts will be set, otherwise, the threshold text boxes will be disabled, and alerts will not take place.

Turnaround Time:

Average Study Completion Time: Setting thresholds for this item will cause the values for "Total Turnaround Time" in the Study Status display (lower grid) to be updated. The user can set the mild threshold (Yellow Alert) for this in milliseconds, which will cause a mild alert to be initiated once the threshold has been surpassed. The user can also set a High threshold (Red Alert), which will cause a severe alert to be called. The value of the High Risk Threshold must be greater than the Mild Risk Threshold. In the illustrated embodiment, the checkbox next to the item must be selected so that alerts will be set, otherwise, the threshold text boxes will be disabled, and alerts will not take place.

Storage Usage:

Available Disk Space: Setting thresholds for this item will cause the values for "Available Storage" in the Status List Overview display to be updated with Yellow and Red highlights. The user can set the mild threshold (Yellow Alert) for this in Megabytes (MB), which will cause a mild alert to be initiated once the threshold has been surpassed. The user can also set a High threshold (Red Alert), which will cause a severe alert to be called. The value of the High Risk Threshold must be smaller than the Mild Risk Threshold. In the illustrated embodiment, the checkbox next to the item must be selected so that alerts will be set, otherwise, the threshold text boxes will be disabled, and alerts will not take place.

In the embodiment illustrated in FIG. 9a, clicking on the System log icon draws up the System logging display. As shown in FIG. 9h, the administrator may be provided with the logging utility to keep track of different events that occur on the system. Such events include successful logins to the system, which will be logged with the username, date, and time of login. Modifications made to any items inside the Manage section may also be logged. Alerts may be logged including the case that occurred, the server that had the alert, and any relevant information. Logging for the display client may be retained for a period of time set by the administrator.

FIG. 9i provides an administrator with a display to manipulate the locations of servers. The administrator is given the option to add/edit/delete locations or their relevant information. The display illustrates a table with the following information:

Name-identifies the name of the location containing servers

Description—contains the description of the location

Address—contains the address of the location

The administrator is allowed to add, edit, and delete locations. By clicking on the "add location" button, the administrator can add a new location. By clicking on the "edit" button, the administrator is allowed to edit information regarding the current location. By clicking on the "delete" button, a confirmation message may appear to delete the current location. Accepting the confirmation would permanently delete the current location.

Another embodiment provides a scalable and customizable system and method for monitoring and analyzing the workflow within and throughout the healthcare enterprise system. Every healthcare enterprise has a unique configuration and workflow information needs. A powerful capability of this embodiment is the ability to customize the system for the configuration of a specific healthcare enterprise and provide information for the customer's desired criteria. The scalability of the embodiment may also be a powerful asset.

The embodiment can be used with small or immensely complex healthcare enterprises. The embodiment can accommodate centralized or distributed archives, servers, modalities, etc. in a healthcare enterprise system. It can easily assimilate new acquisitions in the enterprise, such as new facilities, a new IS system or a new archive.

Another embodiment provides the ability to monitor the performance criteria for the healthcare enterprise established by the user. In addition to displaying performance outside of the performance criteria, this embodiment can also execute alarms. The embodiment can additionally send messages according to the customer's established procedures. For example, when performance of an activity reaches an alarm level, the embodiment may send an e-mail message or a text message to a user specified phone number. The destination of such alerts and messages can be customized and set in the general settings of FIG. 9b.

In another embodiment, specific preset remedial actions may be set by the administrator in advance of potential problems. For example, rules can be customized by the administrator so that if selected thresholds of inefficiency are approached by certain resources, further studies are re-routed to other resources to alleviate the bottleneck. In other instances, identified personnel that are not working efficiently may be immediately alerted to the bottlenecks that they are causing. Such alerts or reprimands could be automatically programmed for delivery by the administrator. Further customization can be accomplished by administration personnel.

There are many other enterprise diagnostic activities that could be monitored by the various embodiments, if all appropriate connections and permissions are made by the administrator. Other embodiments could also show non-diagnostic activities, such as purchasing activities, admitting activities, nurse station activities, any department activities, etc.

Figure 10A:
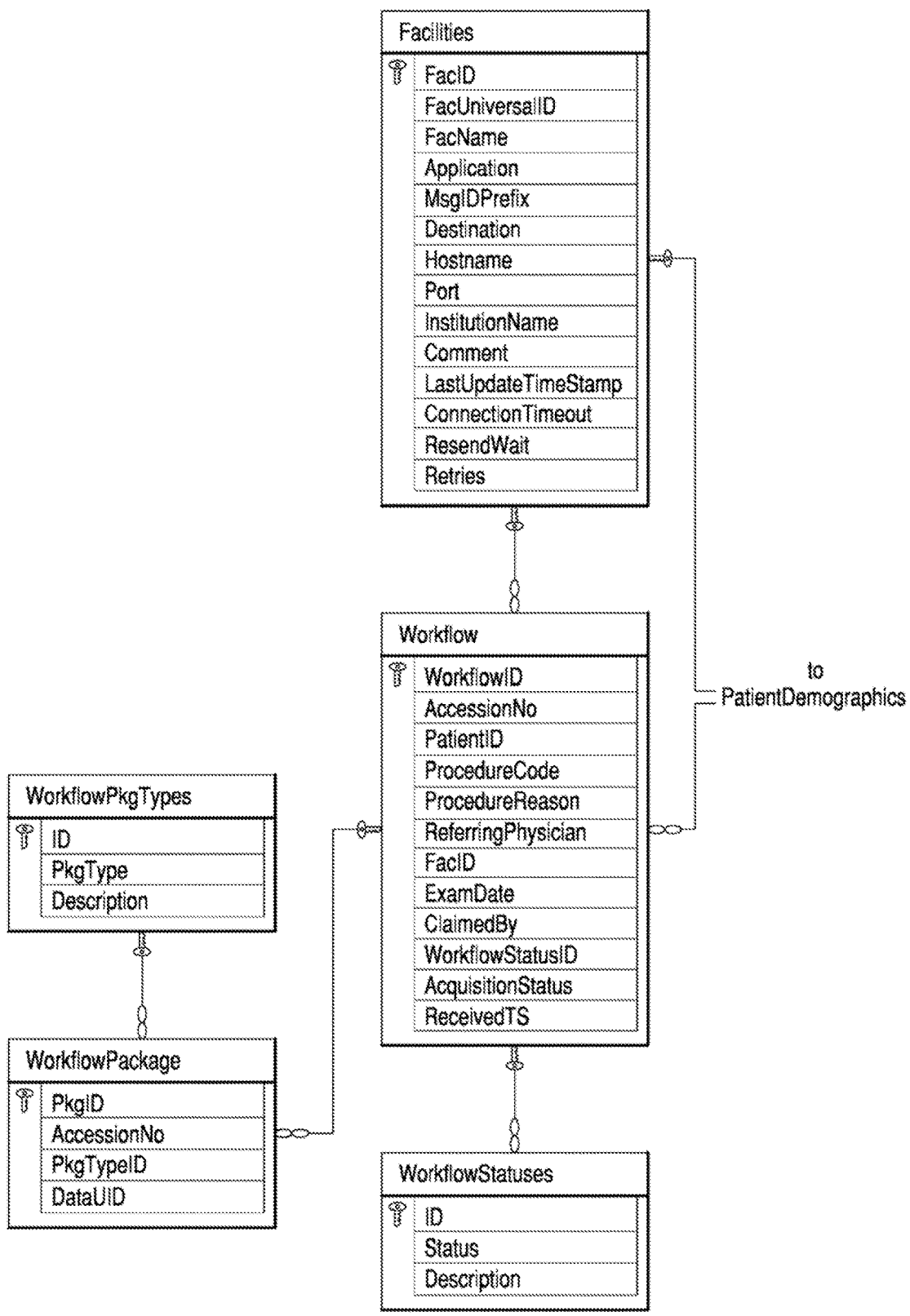
FIGS. 10a through 10e provide data structure diagrams of records of a database which may be used in a specific embodiment.
Figure 10B:
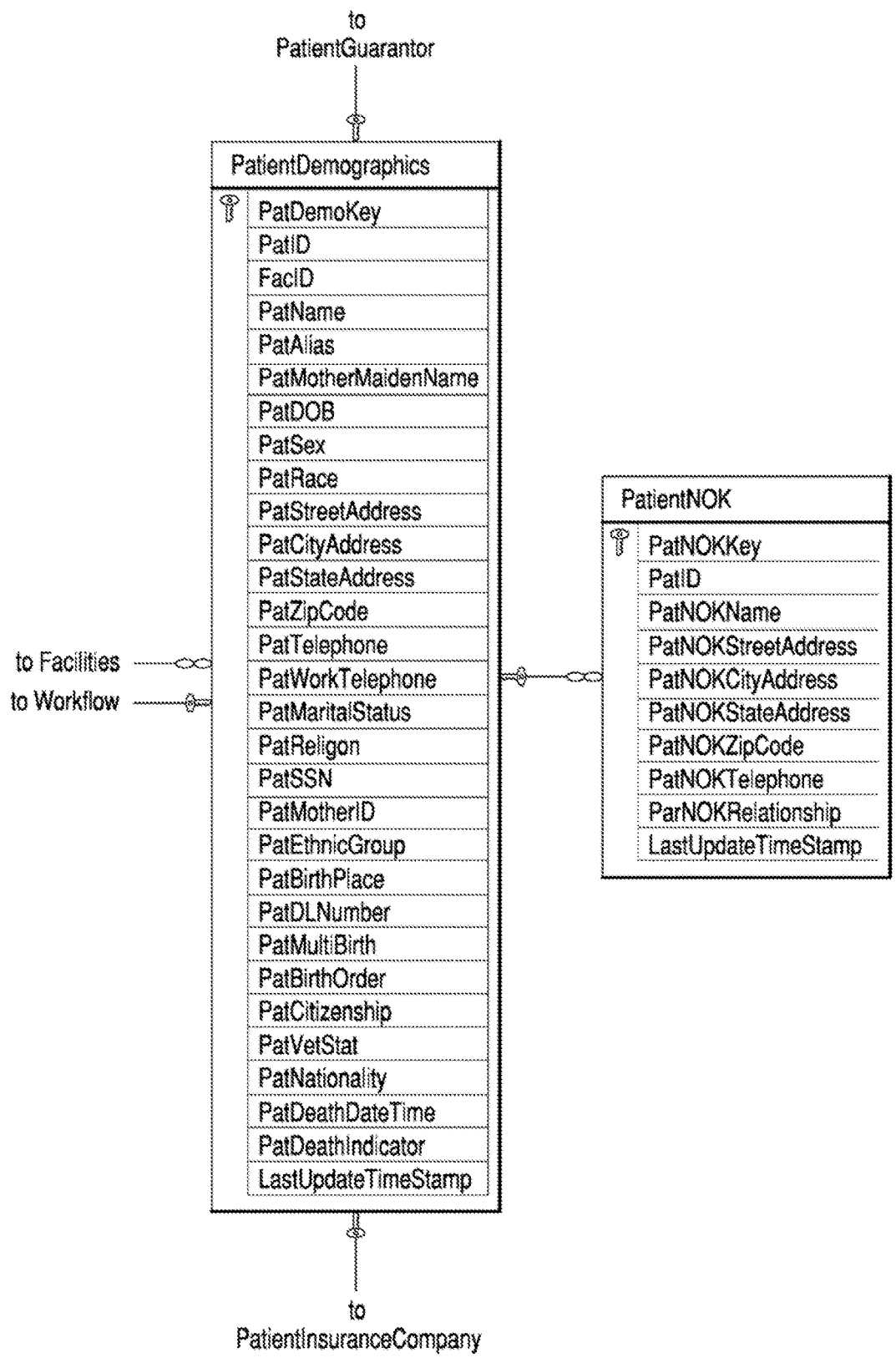
Figure 10C:
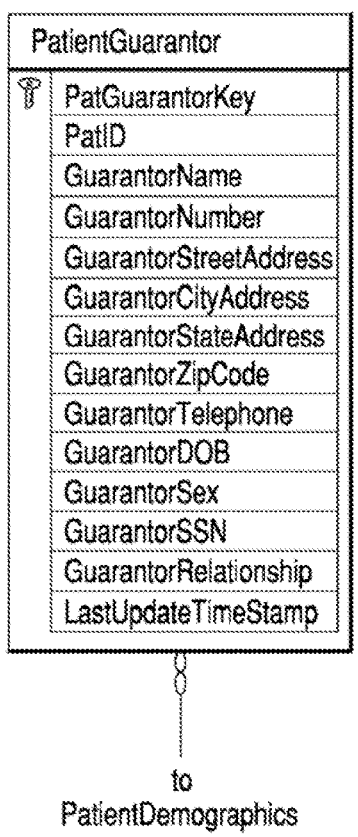
Figure 10D:
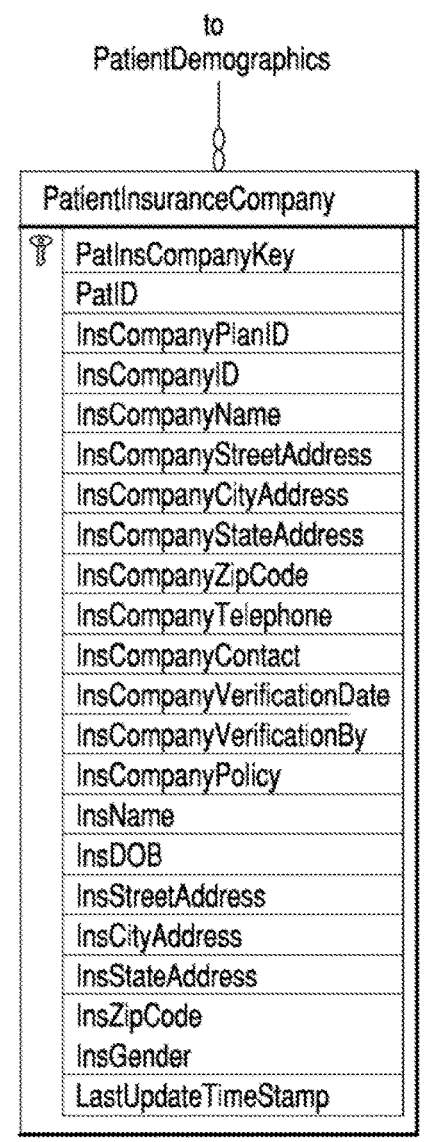
Figure 10E:
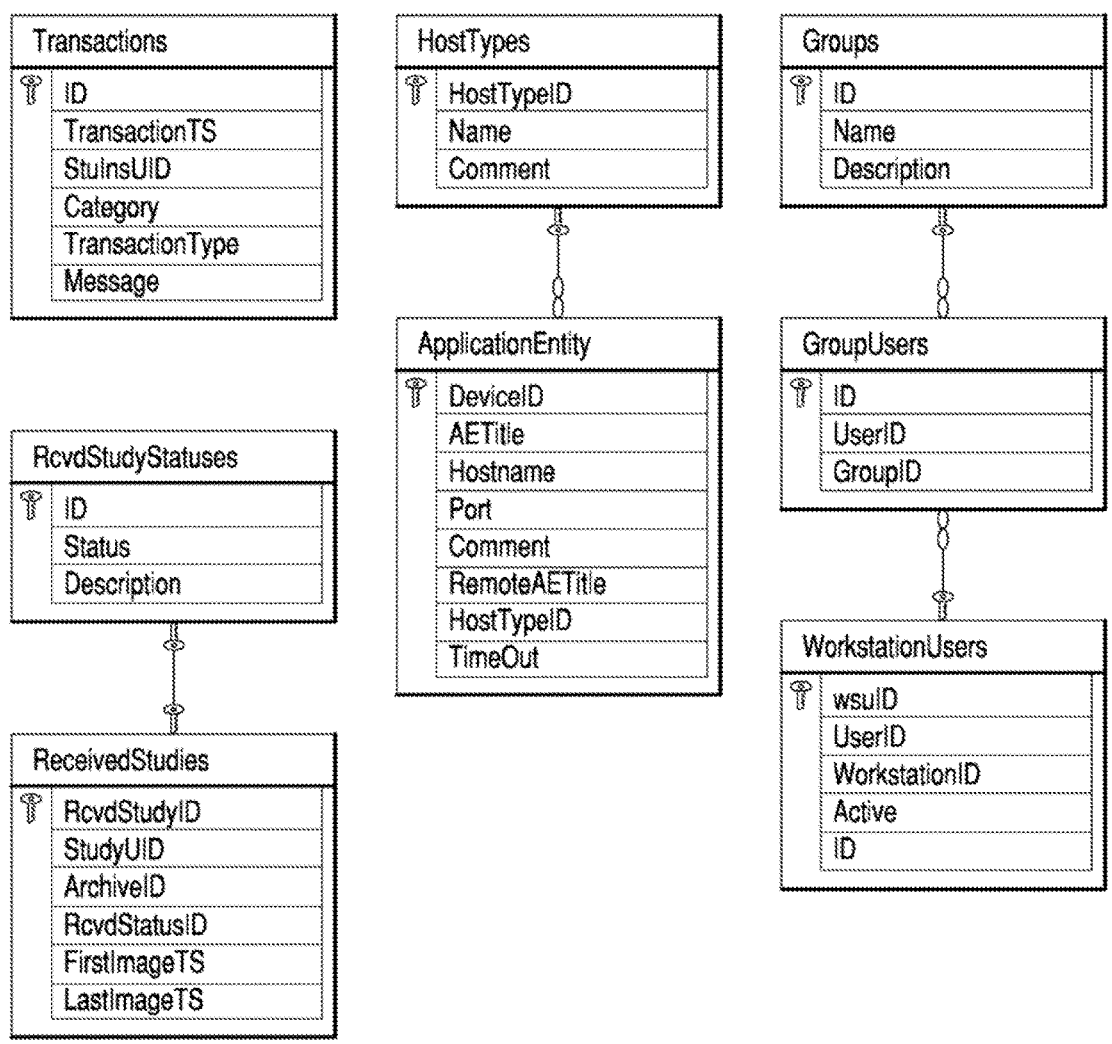

FIGS. 10a-10e provide data structure diagrams for an embodiment of the data records and their specific fields for a database which may be used in a specific embodiment. FIGS. 10c-10e provide close up views of the respective components illustrated in FIGS. 10a-10b showing example data field names associated with each data table.

FIG. 11a-11h provide example data structure diagrams which describe the data records and their specific fields for a database describing routes, destinations, rules, received images, accession destinations, and sent images for one embodiment. The database embodiment illustrated in these figures may be used by the software procedures to operate the enterprise-wide system of worklists.

While the present invention has been disclosed with reference to certain example embodiments, numerous modifications, alterations, and changes to the described embodiments are possible without departing from the sphere and scope of the present invention, as defined in the appended claims. Accordingly, it is intended that the present invention not be limited to the described embodiments, but that it have the full scope defined by the language of the following claims, and equivalents thereof.

We claim:

1. A method for implementing augmented, integrated, interoperable network for monitoring workflow within an integrated healthcare enterprise having a plurality of components and providing remedial measures in response to workflow bottlenecks, comprising:

connecting a data acquisition unit to networks comprising hospital information systems (HIS), radiology information systems (RIS), Picture Archive and Communication Systems (PACS), and other servers and devices of the integrated healthcare enterprise;

routing image studies within the integrated healthcare enterprise according to routing rules associated with each of the image studies;

collecting usage and capacity information for each server of the integrated healthcare enterprise, wherein the usage and capacity information comprises at least one of image study completion rates, image study turn-around time, aging of image studies, and image studies storage information for each server;

collecting workflow information of images studies being sent and received by each server of the integrated healthcare enterprise;

analyzing collected workflow information and usage and capacity information to determine values associated with each server, wherein the values are based on the usage and capacity information;

comparing determined values to predetermined threshold values to identify servers causing workflow bottlenecks; and automatically generating remedial routing rules to route image studies to other servers within the integrated healthcare enterprise.

2. The method of claim 1, wherein usage and capacity information for each server is collected through a Web service running on each server which returns usage and capacity information to the data acquisition unit.

3. The method of claim 1, wherein usage and capacity information for each server is collected through secure shell (ssh) access to each server by the data acquisition unit.

4. The method of claim 1, wherein collecting workflow information comprises the data acquisition unit monitoring, on a fixed interval, the state of images studies being sent and received by each server.

5. The method of claim 1, wherein workflow information for each server is collected through secure shell (ssh) access to each server by the data acquisition unit.

6. The method of claim 1, further comprising:

collecting user information by user name, type or organization association, the usage information selected from the group consisting of login time, login duration, systems accessed, and response time for information requests;

analyzing collected user information to determine user values associated with each server;

comparing determined user values to predetermined threshold user values to identify servers causing workflow bottlenecks; and automatically generating remedial routing rules to route image studies to other servers within the integrated healthcare enterprise.

7. The method of claim 1, wherein the bottlenecks comprise workflow slowdowns and stoppages.

8. A system that implements an augmented, integrated, interoperable network for monitoring workflow within an integrated healthcare enterprise having a plurality of components and providing remedial measures in response to workflow bottlenecks, comprising:

means for connecting a data acquisition unit to networks comprising hospital information systems (HIS), radiology information systems (RIS), Picture Archive and Communication Systems (PACS), and other servers and devices of the integrated healthcare enterprise;

means for routing image studies within the integrated healthcare enterprise according to routing rules associated with each of the image studies;

means for collecting usage and capacity information for each server of the integrated healthcare enterprise wherein the usage and capacity information comprises at least one of image study completion rates, image study turnaround time, aging of image studies and image studies storage information for each server;

means for collecting workflow information of images studies being sent and received by each server of the integrated healthcare enterprise;

means for analyzing collected workflow information and usage and capacity information to determine values associated with each server, wherein the values are based on the usage and capacity information;

means for comparing determined values to predetermined threshold values to identify servers causing workflow bottlenecks; and means for automatically generating remedial routing rules to route image studies to other servers within the integrated healthcare enterprise.

9. The system of claim 8, wherein the means for collecting usage and capacity information for each server comprises a Web service running on each server which returns usage and capacity information to the data acquisition unit.

10. The system of claim 8, wherein the means for collecting usage and capacity information for each server comprises secure shell (ssh) access to each server by the data acquisition unit.

11. The system of claim 8, wherein the means for collecting workflow information comprises means for the data acquisition unit to monitor, on a fixed interval, the state of images studies being sent and received by each server.

12. The system of claim 8, wherein the means for collecting workflow information for each server comprises secure shell (ssh) access to each server by the data acquisition unit.

13. The system of claim 8, further comprising:

means for collecting user information by user name, type or organization association, the usage information selected from the group consisting of login time, login duration, systems accessed, and response time for information requests;

means for analyzing collected user information to determine user values associated with each server;

means for comparing determined user values to predetermined threshold user values to identify servers causing workflow bottlenecks; and means for automatically generating remedial routing rules to route image studies to other servers within the integrated healthcare enterprise.

14. The system of claim 8, wherein the bottlenecks comprise workflow slowdowns and stoppages.

15. A non-transitory computer readable medium having stored thereon computer executable instructions for implementing augmented, integrated, interoperable network for monitoring image study workflow within an integrated healthcare enterprise having a plurality of components and providing remedial measures in response to workflow bottlenecks, the computer executable instructions configured to cause the plurality of components to perform steps comprising:

connecting a data acquisition unit to networks comprising hospital information systems (HIS), radiology information systems (RIS), Picture Archive and Communication Systems (PACS), and other servers and devices of the integrated healthcare enterprise;

routing image studies within the integrated healthcare enterprise according to routing rules associated with each of the image studies;

collecting usage and capacity information for each server of the integrated healthcare enterprise, wherein the usage and capacity information comprises at least one of image study completion rates, image study turnaround time, aging of image studies and image studies storage information for each server;

collecting workflow information of images studies being sent and received by each server of the integrated health care enterprise;

analyzing collected workflow information and usage and capacity information to determine values associated with each server, wherein the values are based on the usage and capacity information;

comparing determined values to predetermined threshold values to identify servers causing workflow bottlenecks; and automatically generating remedial routing rules to route image studies to other servers within the integrated healthcare enterprise.

16. The non-transitory computer readable medium of claim 15, wherein the computer executable instructions further comprise instructions to collect usage and capacity information for each server through a Web service running on each server which returns usage and capacity information to the data acquisition unit.

17. The non-transitory computer readable medium of claim 15, wherein the computer executable instructions further comprise instructions to collect usage and capacity information for each server through secure shell (ssh) access to each server by the data acquisition unit.

18. The non-transitory computer readable medium of claim 15, wherein the computer executable instructions further comprise instructions to collect workflow information by configuring the data acquisition unit to monitor, on a fixed interval, the state of images studies being sent and received by each server.

19. The non-transitory computer readable medium of claim 15, wherein the computer executable instructions further comprise instructions to configure the data acquisition unit to collect workflow information for each server through secure shell (ssh) access to each server.

20. The non-transitory computer readable medium of claim 15, wherein the computer executable instructions further comprise instructions to:
collect user information by user name, type or organization association, the usage information selected from the group consisting of login time, login duration, systems accessed, and response time for information requests;
analyze collected user information to determine user values associated with each server;
compare determined user values to predetermined threshold user values to identify servers causing workflow bottlenecks; and
automatically generate remedial routing rules to route image studies to other servers within the integrated healthcare enterprise.

21. The non-transitory computer readable medium of claim 15, wherein the computer executable instructions are configured to cause the processor to perform operations such that the bottlenecks include workflow slowdowns and stoppages.

* * * * *